(12) United States Patent
Fujiwara et al.

(10) Patent No.: US 9,101,566 B2
(45) Date of Patent: Aug. 11, 2015

(54) FERMENTATION PRODUCT OF CEREAL PLANT-DERIVED MATERIAL AND IMMUNOMODULATOR

(75) Inventors: Daisuke Fujiwara, Yokohama (JP); Masaru Kato, Yokohama (JP); Hideki Koizumi, Yokohama (JP); Kumiko Ikado, Yokohama (JP); Yasuhisa Ano, Yokohama (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 670 days.

(21) Appl. No.: 13/380,763

(22) PCT Filed: Jun. 25, 2010

(86) PCT No.: PCT/JP2010/060807
§ 371 (c)(1),
(2), (4) Date: Dec. 23, 2011

(87) PCT Pub. No.: WO2010/150867
PCT Pub. Date: Dec. 29, 2010

(65) Prior Publication Data
US 2012/0094328 A1    Apr. 19, 2012

(30) Foreign Application Priority Data

Jun. 25, 2009 (JP) ................................ 2009-151023
Dec. 18, 2009 (JP) ................................ 2009-288063

(51) Int. Cl.
| | |
|---|---|
| A61K 31/575 | (2006.01) |
| A61K 36/06 | (2006.01) |
| C12N 5/00 | (2006.01) |
| A23L 1/105 | (2006.01) |
| A23L 1/28 | (2006.01) |
| A23L 1/30 | (2006.01) |
| A23L 2/38 | (2006.01) |
| A61K 36/899 | (2006.01) |

(52) U.S. Cl.
CPC ............... *A61K 36/06* (2013.01); *A23L 1/105* (2013.01); *A23L 1/28* (2013.01); *A23L 1/30* (2013.01); *A23L 1/3002* (2013.01); *A23L 2/38* (2013.01); *A61K 31/575* (2013.01); *A61K 36/899* (2013.01); *A23V 2002/00* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 2004/0028795 A1 | 2/2004 | Doat et al. | |
| 2005/0281898 A1 | 12/2005 | Sugiyama et al. | |
| 2008/0248161 A1* | 10/2008 | Inafuku et al. | 426/52 |

FOREIGN PATENT DOCUMENTS

| | | |
|---|---|---|
| JP | 2005-179315 A | 7/2005 |
| JP | 2006-096703 A | 4/2006 |
| JP | 2008-120739 A | 5/2008 |
| JP | 2008-167660 A | 7/2008 |
| JP | 2009-118783 A | 6/2009 |
| JP | 2009-131171 A | 6/2009 |
| WO | 9944442 | 9/1999 |
| WO | WO 2006/123474 A1 | 11/2006 |
| WO | WO 2006123474 A1 * | 11/2006 |

OTHER PUBLICATIONS

Jefferson et al. (The Journal of Biological Chemistry, vol. 266, No. 9 pp. 5486-5496; 1991).*
Lizée et al. (Nature Immunology, vol. 4, No. 11, pp. 1065-1073; 2003).*
Wüstner et al. (Traffic, vol. 6, pp. 396-412; 2005).*
Li et al., "Two-sided effect of Cordyceps sinensis on dendritic cells in different physiological stages," Journal of Leukocyte Biology, vol. 85, pp. 987-995 (electronically available Mar. 2009).*
Li et al, "Quality control of Cordyceps sinensis, a valued traditional Chinese medicine," Journal of Pharmaceutical and Biomedical Analysis, vol. 41, pp. 1571-1584 (2006).*
Thomson Scientific, Abstract No. XP-002717811 dated Jun. 24, 2002.
Thomson Scientific, Abstract No. XP-002717812 dated Apr. 30, 2008.
Thomson Scientific, Abstract No. XP-002717813 dated Mar. 4, 2003.
Murooka et al., "Traditional healthful fermented products of Japan", Journal of Industrial Microbiology & Biotechnology, 35(8):791-798 (2008).
Zhang et al., "Ergosterimide, a new natural Diels-Alder adduct of a steroid and maleimide in the fungus *Aspergillus niger*", Steroids, 72(9-10):723-727 (2007).
Barton et al., "A new sterol from a strain of *Aspergillus niger*", J. Chemical Society, pp. 2728-2733 (1951).

* cited by examiner

*Primary Examiner* — Cherie M Stanfield
*Assistant Examiner* — Paul D. Pyla
(74) *Attorney, Agent, or Firm* — Sughrue Mion, PLLC

(57) ABSTRACT

The present invention provides dendritic cells (DCs) having reduced inflammatory activity, a method for producing DCs capable of inducing regulatory T cells and regulatory T cells, and substances useful for such a method, wherein the DCs and regulatory T cells are useful for prevention and treatment of immune diseases. The present invention relates to a cereal plant-derived material fermented with a koji microorganism, which is obtained by fermentation thereof with a koji microorganism, or a processed product thereof. Preferably, the fermented product or a processed product thereof comprises 14-dehydroergosterol. According to the present invention, regulatory DCs and regulatory T cells can be induced and the proliferation of inflammatory T cells can be suppressed using plant-derived materials.

3 Claims, 24 Drawing Sheets

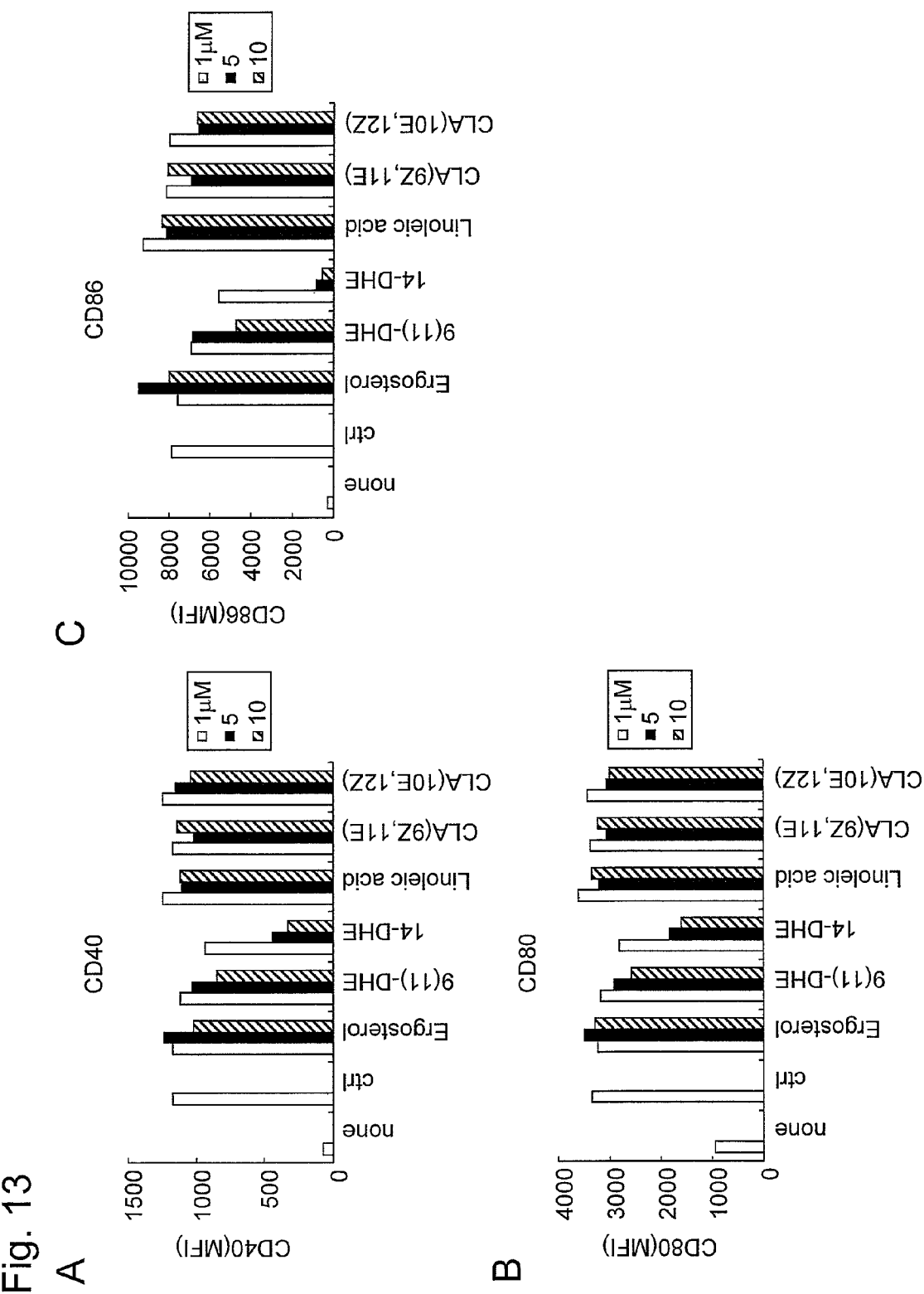

FERMENTATION PRODUCT OF CEREAL PLANT-DERIVED MATERIAL AND IMMUNOMODULATOR

CROSS REFERENCE TO RELATED APPLICATION

This application is a National Stage of International Application No. PCT/JP2010/060807 filed on Jun. 25, 2010, claiming priority based on Japanese Patent Application Nos. 2009-151023, filed Jun. 25, 2009 and JP 2009-288063, filed Dec. 18, 2009, the contents of all of which are incorporated herein by reference in their entirety.

TECHNICAL FIELD

The present invention relates to a cereal plant-derived material fermented with koji or a processed product thereof, and an immunomodulator comprising the fermented product or a processed product thereof. The present invention also relates to a method for producing antigen presenting cells and regulatory T cells, and to a use of a fermented product of a cereal plant-derived material or a processed product thereof, or 14-dehydroergosterol, in the method. The present invention further relates to a use of a fermented product of a cereal plant-derived material or a processed product thereof, or 14-dehydroergosterol, for prevention or treatment of immune diseases.

BACKGROUND ART

Dendritic cells (DCs) compose a group of antigen presenting cells together with B cells and macrophages. Among various antigen presenting cells, DCs are known to have the highest antigen-presenting capacity. DCs stimulate and sensitize the peripheral immune system, which is centered on the acquired immunity mediated by T cells, B cells, NK/NKT cells, and the like, and hence, DCs are thought to function as a director or control tower of the immune system. One of the central roles of DCs is to induce the acquired immune system by incorporating foreign matter from outside the body, antigen proteins in the body, and the like, degrading them, and then presenting them as antigens. With another function of DCs, DCs respond to inflammatory stimuli, so as to produce various inflammatory cytokines.

Various immune diseases (e.g., allergies, autoimmune diseases, and enteritis) are currently increasing explosively around the world. As a cause of such a phenomenon, a hygiene hypothesis or the like focusing on changes in enteric bacterial balance has been proposed, but no established theory exists. However, it has been confirmed that such immune diseases share common characteristics such as increases in production of inflammatory cytokines including TNF-α, IL-6, IL-12, IL-17, and the like. Suppression of inflammatory immune cells that proliferate in response to the production and the stimulation of cytokines are expected to be effective for prevention and treatment of these immune diseases. Actually, it has been progressively reported that antibodies targeting the aforementioned cytokines exhibit significant effects in humans.

It is known that a proinflammatory irritant represented by LPS (lipopolysaccharide) is recognized by a toll-like receptor (TLR) on DCs, so as to cause activation and/or maturation of DCs, inducing inflammatory response through the release of various inflammatory cytokines and chemokines. It has been reported that in many immune diseases, abnormal activation of DCs, macrophages, and the like takes place in the natural immune system. Therefore, methods for suppressing such activation of the natural immune system and substances that can suppress the activation of the natural immune system are very effective for prevention and treatment of the above immune diseases.

As agents for inducing DCs exhibiting reduced inflammatory activity, IL-10/TGF-β, rapamycin, vasoactive intestinal peptide (VIP), and the like are currently known. However, these drugs also have many other biological effects, so that the administration thereof to human bodies for prevention and treatment of immune diseases is unrealistic. Hence, a possible method for the use of these agents for prevention and treatment of immune diseases is an ex vivo method that comprises inducing DCs, which have reduced inflammatory activity, from collected blood in vitro, and then returning the DCs to a human body.

An immunosuppressive agent such as FK506 is used to suppress rejection that poses a problem upon tissue or organ transplantation. However, adverse reactions due to nonspecific immunosuppression by existing drugs have been questioned. It has been revealed that regulatory T cells (Treg) in addition to immunosuppressive agents are useful to suppress rejection at the time of transplantation. Treg is known to be induced via secretion of a cytokine from DCs. Therefore, if a method for inducing DCs capable of resulting in production of Treg and a method for directly inducing Treg from naive T cells are developed, such methods could be expected to be useful for suppression of rejection upon transplantation.

In recent studies, retinoic acid, 1,25-dihydroxy vitamin D3, and the like have been rediscovered as substances capable of directly acting on $CD4^+$ T cells so as to induce Treg. These substances are thought to be useful in terms of anti-inflammatory effects, suppression of graft rejection, and the like, similarly to substances that induce DCs exhibiting reduced inflammatory activity.

Patent Literature 1 describes immunopotentiators obtained from fermentation-degraded products which are produced by fermentation of soybean, wheat, rice, or a material containing byproducts thereof using filamentous fungi or an enzyme(s) obtained therefrom. Specifically, patent Literature 1 demonstrates that glucose consumption by macrophages is enhanced by a substance that is obtained by separating an ethanol-insoluble fraction from a fermented product obtained by fermentation of a soybean-derived material or wheat using *Aspergillus oryzae* or *Aspergillus sojae* and then further extracting a high-molecular-weight fraction from the above ethanol-insoluble fraction.

Patent Literature 2 describes a macrophage-activating agent obtained by fermentation of a soybean-derived material using lactic acid bacteria.

Patent Literature 3 describes hyaluronidase inhibition, antiallergic activity, and an immunostimulating substance obtained from fermentation-degraded products which are produced by fermentation of soybean, wheat, citrus fruits, fruits, or a material containing a processed product thereof using filamentous fungi, *Bacillus subtilis* natto, or an enzyme(s) obtained therefrom. Patent Literature 3 describes that a substance obtained by fermentation of a soybean-derived material or wheat using *Aspergillus oryzae*, separation of an ethanol-insoluble fraction from the fermented product, and then extraction a high-molecular-weight fraction from the ethanol-insoluble fraction has hyaluronidase-inhibiting activity and immunostimulating activity as determined using IgA production from Peyer's patch cells as an indicator.

Patent Literature 4 describes an immunostimulating substance obtained by fermentation of a plant component such as wheat flour using *Pantoea agglomerans*, which is a Gram-negative bacterium.

Patent Literature 5 describes that a fermented product obtained by fermenting a mixture of a product obtained by means of steam blasting treatment, such as bagasse, and wheat bran using *Aspergillus sojae* comprises xylobiose- and xylotriose-rich xylo-oligosaccharides and a substance(s) with antioxidation activity.

PRIOR ART LITERATURES

Patent Literatures

Patent Literature 1: Japanese Patent Publication (Kokai) No. 2005-179315 A

Patent Literature 2: Japanese Patent Publication (Kokai) No. 2003-73293 A

Patent Literature 3: International Patent Publication No. WO 2005/030938 pamphlet Patent Literature 4: Japanese Patent Publication (Kokai) No. 2007-202562 A Patent Literature 5: International Patent Publication No. WO 2006/123474 pamphlet

SUMMARY OF THE INVENTION

Problem to be Solved by the Invention

As described above, a method for inducing DCs having reduced inflammatory activity, a method for inducing Treg through induction of DCs capable of resulting in production of Treg, a method for directly inducing Treg from naive T cells, a method for suppressing the proliferation of inflammatory T cells, and substances useful for these methods, have been desired.

Means for Solving the Problem

As a result of intensive studies for solving such problems, the present inventors have now found that a cereal plant-derived material, and in particular, a material fermented by acting an Koji microorganism on wheat bran or a processed product thereof (hereinafter, referred to as "a fermented product of a cereal plant plant-derived material," "a processed fermented product of a cereal plant-derived material," or "a fermented product of a cereal plant-derived material or a processed product thereof") can solve the above problems, thereby leading to completion of the present invention as described below.

Specifically, the present invention has the following features.

(1) A fermented product of a cereal plant-derived material or a processed product thereof, which is obtained by fermenting a cereal plant-derived material using a koji microorganism.

(2) The fermented product or a processed product thereof according to (1) above, wherein the cereal plant-derived material comprises a cereal plant seed coat.

(3) The fermented product or a processed product thereof according to (1) or (2) above, wherein one or more cereal plants are selected from the family Gramineae (Poaceae).

(4) The fermented product or a processed product thereof according to any one of (1) to (3) above, wherein the cereal plant is wheat.

(5) The fermented product or a processed product thereof according to any one of (1) to (4) above, wherein the koji microorganism is a filamentous fungus of the genus *Aspergillus*.

(6) The fermented product or a processed product thereof according to any one of (1) to (5) above, wherein the koji microorganism is black koji.

(7) The fermented product or a processed product thereof according to any one of (1) to (6) above, which is further subjected to separation of an ethanol-soluble fraction by ethanol extraction after fermentation.

(8) The fermented product or a processed product thereof according to (7) above, which is further subjected to separation of a hexane-soluble fraction by hexane fractionation following ethanol extraction.

(9) The fermented product or a processed product thereof according to any one of (1) to (8) above, which comprises 14-dehydroergosterol.

(10) The fermented product or a processed product thereof according to any one of (1) to (9) above, which has an effect of modifying an antigen presenting cell.

(11) A composition for modifying antigen presenting cells, which comprises the fermented product or a processed product thereof according to any one of (1) to (10) above.

(12) A beverage or a food, which comprises the fermented product or a processed product thereof according to any one of (1) to (10) above.

(13) An immunomodulator, which comprises the fermented product or a processed product thereof according to any one of (1) to (10) above.

(14) A method for preparing a processed fermented product of a cereal plant-derived material, comprising the steps of fermenting a cereal plant-derived material using a koji microorganism, subjecting the fermented product to ethanol extraction, and subjecting the ethanol extract to hexane fractionation.

(15) The method according to (14) above, wherein the cereal plant-derived material comprises a cereal plant seed coat.

(16) The method according to (14) or (15) above, wherein one or more cereal plants are selected from the family Gramineae (Poaceae).

(17) The method according to any one of (14) to (16) above, wherein the cereal plant is wheat.

(18) The method according to any one of (14) to (17) above, wherein the koji microorganism is a filamentous fungus of the genus *Aspergillus*.

(19) The method according to any one of (14) to (18) above, wherein the koji microorganism is a black koji microorganism.

(20) A method for modifying an antigen presenting cell, comprising a step of bringing the fermented product or a processed product thereof according to any one of (1) to (10) above into contact with the cell which is from a subject.

(21) A method for producing a regulatory dendritic cell, comprising a step of bringing the fermented product or a processed product thereof according to any one of (1) to (10) above into contact with a dendritic cell which is from a subject.

(22) A pharmaceutical composition for prevention or treatment of an immune disease, which comprises the fermented product or a processed product thereof according to any one of (1) to (10) above.

(23) An immunomodulator comprising 14-dehydroergosterol.

(24) A method for modifying an antigen presenting cell, which comprises a step of bringing 14-dehydroergosterol into contact with the cell which is from a subject.

(25) A method for producing a regulatory dendritic cell, which comprises a step of bringing 14-dehydroergosterol into contact with a dendritic cell which is from a subject.

(26) A pharmaceutical composition for prevention or treatment of an immune disease, which comprises 14-dehydroergosterol.

(27) A koji-fermented product or a processed product thereof, which comprises 14-dehydroergosterol and has an effect of modifying antigen presenting cells.

(28) A composition, which comprises the koji-fermented product or a processed product thereof according to (27) above.

(29) A method for producing a regulatory T cell, which comprises a step of bringing the fermented product or a processed product thereof according to any one of (1) to (10) above into contact with a cell which is from a subject.

(30) A method for producing a regulatory T cell, which comprises a step of bringing 14-dehydroergosterol into contact with a cell which is from a subject.

(31) An agent for regulatory T cell induction comprising 14-dehydroergosterol.

(32) An agent for suppression of inflammatory T cell proliferation comprising 14-dehydroergosterol.

This description includes part or all of the contents as disclosed in the specification and/or drawings of Japanese Patent Application No. 2009-288063, from which the present application claims the priority.

Effect of the Invention

According to the present invention, novel materials or substances having preventive and therapeutic effects against graft rejection and immune diseases including graft-versus-host disease by enhancing immunological tolerance are provided.

BRIEF DESCRIPTION OF THE DRAWINGS

FIG. 16A shows the results of MLR; and FIG. 16B shows the results of antigen-specific T-cell reaction. The amount of each cytokine in culture supernatant was measured by ELISA.

FIG. 17 shows the induction of $CD8^+$Treg by DCs treated with 14-DHE and control DCs not treated with the same in the presence of TGF-β.

FIG. 18 shows the induction of $CD4^+$Treg from $CD4^+$T cells in the presence of TGF-β.

FIG. 19A shows the results of the timing for exhibition of the effect and FIG. 19B shows the duration of the effectiveness.

FIG. 20A shows the effect on disease score, and FIG. 20B shows the effect on the amounts of inflammatory cytokines (upper panel: TNF-α; lower panel: IFN-γ) produced by re-stimulation with MOG antigen. LN denotes a regional lymph node, and SPN denotes spleen cell. FIG. 20C shows the proportion of each cytokine producing-positive cell in $CD4^+$ T cells upon re-stimulation with MOG antigen, and FIG. 20D shows the proportion of proliferating CD4+ T cells upon re-stimulation with MOG antigen. FIG. 20E shows the positive rate of an mDC (CD11b+CD11c+B220−) activation marker in the regional lymph node and the spinal cord (upper panel: lymph node; lower panel: spinal cord).

FIG. 21A shows HLA-DR expression; FIG. 21B shows CD80 expression; and FIG. 21C shows CD86 expression.

MODE FOR CARRYING OUT THE INVENTION

Figure 1:
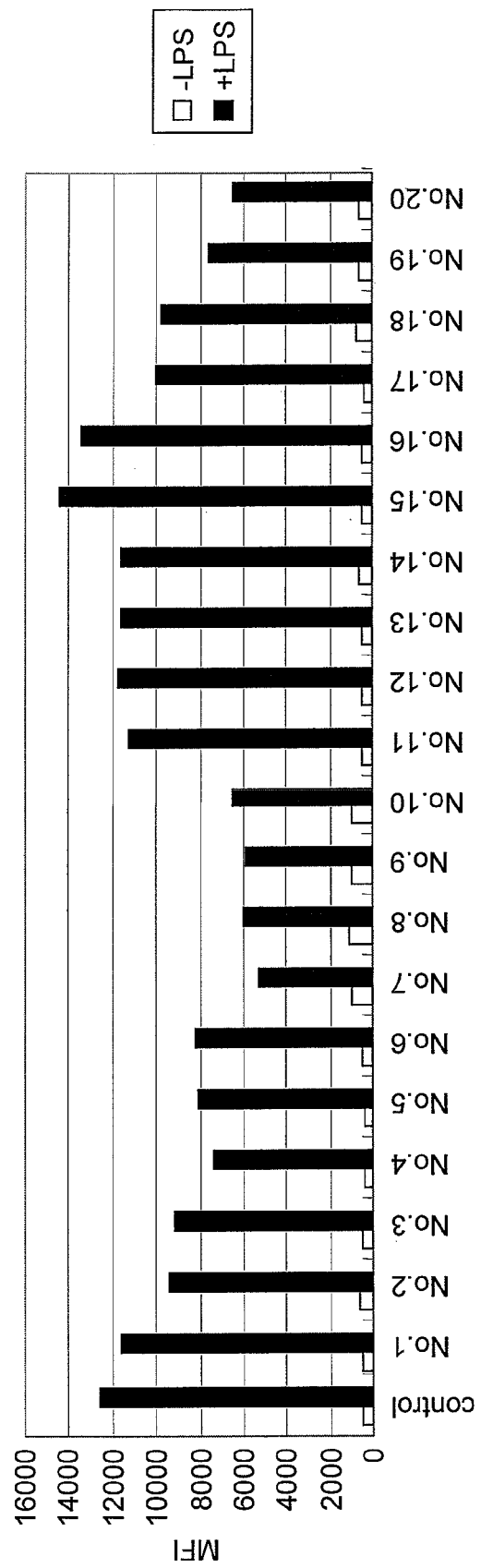
FIG. 1 is the graph showing the effects (i.e., CD86 expression intensity) of different cereal plant-derived materials fermented with koji or processed products thereof on DC differentiation.

The present invention relates to a fermented product of a cereal plant-derived material or a processed product thereof, which is obtained by fermenting the cereal plant-derived material using an Koji microorganism. The present invention also relates to a method for producing antigen presenting cells or regulatory T cells, and to the use of the fermented product of a cereal plant-derived material or a processed product thereof, or 14-dehydroergosterol, in said method. The present invention further relates to the use of a fermented product of a cereal plant-derived material or a processed product thereof, or 14-dehydroergosterol, for prevention or treatment of immune diseases.

The fermented product of a cereal plant-derived material or a processed product thereof of the invention can be obtained by adding an Koji microorganism to a cereal plant-derived material used as a raw material so that the fermentation of interest occurs. The term "a fermented product of a cereal plant-derived material or a processed product thereof" means including both a cereal plant-derived material that has been fermented using an Koji microorganism, and a portion of the fermented material (such as a solvent-extracted fraction). Also, the term "a fermented product of a cereal plant-derived material" may also be used to mean both a fermented cereal plant-derived material and a processed product thereof.

Preferable examples of the cereal plant include all plants classified as Gramineae (Poaceae) plants listed in the plant classification table. Specific examples thereof include, but are not limited to, rice, barley, wheat, rye, foxtail millet, Japanese millet, and corn. Of them, rice, barley, wheat, and rye are preferably used, and in particular wheat is preferably used.

The cereal plant-derived material usable in the invention is a material(s) from cereal plant seeds, typically being the whole seed of a cereal plant or a portion of the seed.

The cereal plant-derived material usable in the invention preferably contains a seed coat. Examples of the cereal plant-derived material containing such seed coat include the whole grain flour of a cereal plant, bran of a cereal plant, rice bran, and the like. Particularly preferable examples of the cereal plant-derived material include the bran of a cereal plant, most preferably wheat bran.

The bran of a cereal plant can be obtained by pulverizing or polishing cereal plant seeds and then recovering the thus obtained external parts of the seeds.

Examples of the koji microorganism usable in the invention include, but are not particularly limited as long as it is possible to ferment a cereal plant-derived material usable in the invention, preferably black koji microorganisms (e.g., *Aspergillus awamori* and *Aspergillus niger*), yellow koji microorganisms (e.g., *Aspergillus oryzae*), red koji microorganisms (e.g., *Monascus anka*), *Aspergillus* microorganisms for shoyu (soy sauce) (e.g., *Aspergillus sojae*), white koji microorganisms (e.g., *Aspergillus kawachii*), and tempeh molds (e.g., *Rhizopus oligosporus*). Preferably, the koji microorganism is a filamentous fungus of the genus *Aspergillus*, and is most preferably a black koji microorganism.

Examples of the Black koji microorganism usable in the invention include *Aspergillus awamori* and *Aspergillus niger* that are classified into black koji molds in a limited sense, *Aspergillus kawachii* that is referred to as white koji mold in a limited sense, and subspecies thereof that are derived from the above-mentioned microorganism strains. These koji microorganism starters are available from Akita Konno Shoten (Japan), Higuchi Moyashi (Higuchi Matsunosuke Shouten, Japan), Nihon Jozo Kogyo (Japan), and the like.

According to the present invention, the fermentation can be performed by using any of the methods known in the art, which comprise inoculating a koji microorganism into a raw material for culture. Examples of the methods used in Japan include a futa (lid)-koji method, a hako (box)-koji method, a yuka (floor)-koji method, and a kikai (mechanical)-koji method.

Regarding the amount of koji to be added to a cereal plant-derived material to which water has been added for treatment (e.g., autoclave, steaming, etc.), the amount of a koji mold starter preferably ranges from 0.005 to 5% by weight, more preferably from 0.01 to 1% by weight, more preferably from 0.05 to 0.5% by weight, and most preferably 0.1% by weight.

The temperature for fermentation slightly differs depending on types of koji microorganisms to be used and generally ranges from 20° C. to 50° C., preferably from 22° C. to 45° C., and more preferably from 30° C. to 40° C. The time for fermentation ranges from 24 hours to 14 days, preferably from 48 hours to 10 days, and more preferably from 72 hours to 7 days, for example. During fermentation, the "teire" (which is a treatment for disintegrating aggregated koji) is preferably performed at certain intervals (e.g., every 24 hours).

The details of the fermentation method are described in the "Fermentation Handbook" (edited by Fermentation and Metabolism Research Group, Japan Bioindustry Association, Japan, 2001), for example.

The humidity during fermentation can be appropriately regulated by a person skilled in the art according to the types of koji microorganisms. For example, during fermentation, relative humidity is maintained at 80% or more. Alternatively, fermentation is performed by maintaining relative humidity at a higher level (e.g., 90% or more) at the initial stage and slightly lowering the relative humidity (e.g., 75% or more) during the late stage (e.g., at and after 24 hours after inoculation of a koji microorganism).

As used herein, the fermented product of a cereal plant-derived material or a processed product thereof includes a fermented cereal plant-derived material or a fraction obtained therefrom through solvent extraction or the like. The extract from the fermented material can be obtained by any of the extraction methods known in the art. Examples of the extraction methods include an organic solvent extraction method, a supercritical-fluid extraction method, and a method for extraction by heating and pressurization. The above exemplified extraction methods can be used alone or in combination.

Solvent extraction can be performed by a general technique known in the art. Examples of an organic solvent that can be used for solvent extraction include, but are not limited to, ethanol, methanol, n-propanol, isopropanol, methyl acetate, ethyl acetate, acetone, hexane, heptane, cyclohexane, benzene, toluene, and phenol. Preferable examples of the organic solvent include ethanol, methanol, ethyl acetate, and hexane. Two or more organic solvents may be mixed before use. Alternatively, the solvent extraction step may be performed, comprising two or more stages in which two or more organic solvents are used.

Specifically, the solvent extraction can be performed, for example, by pulverizing a fermented material previously dried by lyophillization, then adding an organic solvent, and subjecting the mixture to ultrasonication with agitating at a temperature of 20° C. to 50° C., preferably 25° C. to 45° C. The amount of a solvent to be added is 1- to 50-fold, preferably 2- to 40-fold, more preferably 10- to 30-fold the weight of the fermented material. The time for extraction is from 10 minutes to 2 hours, preferably from 15 minutes to 1 hour, and more preferably from 20 minutes to 50 minutes. Subsequently, a filtrate is recovered by filtration, centrifugation, or the like, an insoluble fraction contained in the residue is removed, an organic solvent fraction from the filtrate (that is, an extracted fraction) is concentrated by vacuum evaporation, for example, and thus the extract can be obtained in a fluid form or dried form. Also, the insoluble fraction obtained after organic solvent extraction is repeatedly extracted with an organic solvent, so that organic solvent fractions can be further obtained from the residue after the first organic solvent extraction.

Following the solvent extraction, further fractionation using another solvent may also be performed. For example, a second organic solvent that is the same as or different from that used in solvent extraction is added to the organic solvent fraction obtained by solvent extraction, and then a third organic solvent that is immiscible with the second organic solvent is added to the mixture for extraction, so that a fraction soluble in the third organic solvent can be obtained.

Substances existing in the organic solvent fractions can further be purified. In this case, purification can be performed by an appropriate combination of known separation and purification methods. For example, liquid-liquid distribution, organic solvent precipitation, various types of column chromatography (e.g., HPLC, silica gel chromatography, molecular sieve chromatography, ion exchange chromatography, and reverse phase chromatography), crystallization, and the like can be employed.

Preferably, the fermented product of a cereal plant-derived material or a processed product thereof is an ethanol fraction obtained by separating an ethanol-soluble fraction by ethanol extraction after fermentation. More preferably, the fermented product of a cereal plant-derived material of the invention is a hexane fraction obtained by further separating a hexane-soluble fraction by hexane fractionation after ethanol extraction.

The fermented product of a cereal plant-derived material or a processed product thereof of the invention, which can be obtained in the manner as described above, has an effect of suppressing the immune reaction mediated by DCs, as described later in the Examples. Therefore, the fermented product of a cereal plant-derived material or a processed product thereof is useful for prevention and treatment of immune diseases that are thought to be caused by excessive activation of the immune system.

DCs play a central role in immune responses. Hence, it is expected to realize a novel therapeutic method for suppressing various diseases caused by immune responses mediated by DCs through the use of the fermented product of a cereal plant-derived material or a processed product thereof of the present invention. Examples of diseases to be subjected to the therapeutic method using the present invention include: graft rejection and graft-versus-host disease accompanied with cell grafting or organ or tissue grafting; autoimmune diseases such as rheumatoid arthritis, multiple sclerosis, type I diabetes mellitus, uveitis, autoimmune myocarditis, myasthenia gravis, systemic lupus erythematodes, autoimmune hemolytic anemia, systemic sclerosis, ulcerative colitis, Crohn's disease, Sjogren's syndrome, autoimmune hepatic disease (e.g., primary biliary cirrhosis), psoriasis, idiopathic thrombocytopenic purpura, Goodpasture's syndrome (e.g., glomerulonephritis), pernicious anemia, Hashimoto's disease, leukoderma vulgaris, Behchet's disease, autoimmune gastritis, pemphigus, Guillain-Barre syndrome, and HTLV-1-associated myelopathy; and allergic diseases such as contact hypersensitivity, allergic rhinitis, food allergy, and asthma.

Immune disease-associated inflammation can be improved by oral ingestion of the fermented product of a cereal plant-derived material of the present invention. Further, the onset of an immune disease can be prevented by daily ingestion of the fermented product. For this purpose, the dose of the fermented product of a cereal plant-derived material or a processed product thereof of the present invention per day is preferably 2 g or more, and preferably 10 g or more. The fermented product of a cereal plant-derived material or a processed product thereof is an ingredient obtained by fermenting a cereal plant-derived material with an edible koji microorganism, and thus can be taken to daily dietary life. Furthermore, the time for administration or ingestion thereof may be any time of before meal, between meals, or after meal.

The fermented product of a cereal plant-derived material or a processed product thereof of the present invention can be provided by incorporating it in specific compositions, such as foodstuffs or beverages or pharmaceutical preparations.

When the fermented product of a cereal plant-derived material or a processed product thereof of the present invention is incorporated into foodstuffs or beverages, this product may be processed into any form of foods. Examples of the foodstuffs or beverages, in which the fermented product of a cereal plant-derived material or a processed product thereof of the invention is incorporated, include foodstuffs or beverages such as natural products and processed products thereof. Furthermore, the fermented product of a cereal plant-derived material or a processed product thereof of the invention can be contained in an amount of 10 g or more relative to 100 g of a foodstuff or beverage.

Examples of the foodstuffs or beverages include, but are not limited to, functional foods such as tablet foods, powdery foods, granular foods, capsule foods, and jelly foods, processed cereal plant products such as breads, confectionaries, cookies, and biscuits, dairy products such as milk, yogurt, and ice cream, beverages such as carbonated drinks, soft drinks, fruit juice-containing beverages, and medicinal drinks, prepared foods, and processed foods.

When the fermented product of a cereal plant-derived material or a processed product thereof of the present invention is contained in pharmaceutical preparations, the product can be formulated into immunomodulator for treating, improving, or preventing immune diseases. Examples of administration routes of a preparation include, but are not particularly limited to, oral administration and enteral administration. In the case of oral or enteral administration, the fermented product of a cereal plant-derived material or a processed product thereof may be directly administered to a subject. Alternatively, the fermented product of a cereal plant-derived material or a processed product thereof may be administered to a subject in the form of solutions, suspensions, powders, granules, tablets, or capsules, which are prepared using a pharmaceutically acceptable carrier or excipient.

Examples of the pharmaceutically acceptable carrier or excipient may include, but are not limited to, saccharides such as lactose, sucrose, and dextrose, starch, inorganic materials such as calcium carbonate and calcium sulfate, crystalline cellulose, distilled water, purified water, and oils such as sesame oil, soybean oil, corn oil, olive oil, and cotton seed oil, which are generally used. Furthermore, in addition to such a carrier or an excipient, additives such as a binder, a lubricant, a dispersant, a suspension, an emulsifier, a diluent, a buffer, an antioxidant, and an antibacterial agent may be used in the preparation of immunomodulator of the present invention. The above preparation may be mixed with another pharmaceutical preparation or used in combination with the same. Furthermore, the preparation may be subjected to sterilization treatment.

Examples of the subject to which the immunoregulatory foodstuffs or beverages or the immunomodulator of the present invention is applied include, but are not particularly limited, any of healthy subjects, patients with immune disease, patients with immune diseases under therapy, and healthy subjects who wish to prevent the onset of immune diseases, for example. Such subjects are not limited to humans and may be animals other than humans.

The immunoregulatory foodstuffs or beverages or the immunomodulator of the present invention modifies antigen presenting cells, thereby enabling the induction of regulatory T cells by the thus modified antigen presenting cells. The immunoregulatory foodstuffs or beverages or the immunomodulator of the present invention can also directly induce regulatory T cells. Furthermore, the immunoregulatory foodstuffs or beverages or the immunomodulator of the present invention can suppress inflammatory T cell proliferation, thereby making it possible to suppress excessive immune reaction.

The dosage of the immunoregulatory foodstuffs or beverages or the immunomodulator of the present invention varies depending on various factors such as age, body weight, sex, and the degree of obesity of a subject; however, typically the dosage can be determined so that the amount of the fermented product of a cereal plant-derived material or a processed product thereof of the invention administered per day is 2 g or more and preferably 10 g or more. The interval of administration is not particularly limited.

The fermented product of a cereal plant-derived material or a processed product thereof of the present invention can efficiently improve immune diseases and is an ingredient obtained by fermenting a cereal plant using an edible koji microorganism. Hence, the product has high safety and is useful for use in foodstuffs or beverages or medicaments. Furthermore, the fermented product of a cereal plant-derived material or a processed product thereof of the present invention can be produced from a relatively inexpensive raw material such as wheat bran, and thus is excellent in terms of cost.

The present invention also relates to a pharmaceutical composition for prevention or treatment of immune diseases, comprising the fermented product of a cereal plant-derived material or a processed product thereof of the present invention. The pharmaceutical composition may contain, in addition to the fermented product of a cereal plant-derived material or a processed product thereof of the present invention, the above pharmaceutically acceptable additional ingredients such as an excipient.

The present invention also relates to a method for preparing the processed fermented product of the cereal plant-derived material, which comprises the following steps of: fermenting a cereal plant-derived material using a koji microorganism, extracting the fermented product with ethanol, and fractionating the ethanol extract with hexane. The fermentation method and the solvent extraction method can be performed as described above.

The present invention further relates to a method for modifying antigen presenting cells, which comprises a step of bringing the fermented product of a cereal plant-derived material or a processed product thereof into contact with certain cells collected from a subject.

As used herein, the term "antigen presenting cell" refers to a cell expressing MHC class II on the cell surface, such as dendritic cell (DC), monocyte, macrophage, or B cell, and an undifferentiated cell capable of differentiating into such cell. Preferably, the antigen presenting cell is a dendritic cell.

As described in the Examples below, DCs modified by the method of the present invention exhibit production of activated cell surface markers and inflammatory cytokines at reduced levels and are capable of inducing regulatory T cells (Treg). Therefore, DCs modified by the method of the present invention are useful for prevention and treatment of immune diseases which are thought to be caused by excessive activation of the immune system. Antigen presenting cells modified by the method of the present invention are particularly very useful in an ex vivo therapy that comprises treating cells recovered from a subject by the method of the present invention to obtain regulatory DCs and then returning the regulatory DCs to the subject.

As used herein, the term "modifying antigen presenting cell" means to alter the gene expression (of cell surface markers, cytokines, etc.) in antigen presenting cells, thereby changing the effect on other cells such as T cell. In this case, the gene expression is understood to mean not only mRNA transcription from chromosomal DNA of cells and translation of mRNA to a protein, but also maturation by posttranslational modification of an expressed protein, altered intracellular location of a protein, change in protein secretion from cells, and the like. Preferably, the antigen presenting cells modified by the method of the present invention are capable of inducing regulatory T cells.

The present invention also relates to a method for producing regulatory dendritic cells, which comprises a step of bringing the fermented product of a cereal plant-derived material or a processed product thereof of the present invention into contact with dendritic cells collected from a subject.

As used herein, the term "regulatory dendritic cell" refers to a dendritic cell capable of suppressing excessive activation and/or runaway of the immune system through its own effect and induction of regulatory T cell. Regulatory dendritic cells are differently defined depending on literatures and are not unambiguously defined. Nevertheless, the regulatory dendritic cells are characterized, for example, by: decreased expression levels of CD40, CD80, CD86, MHC class II, and the like that are dendritic cell activation markers; expression of suppressor dendritic cell markers such as ICOSL and PD-L1; decreased production of inflammatory cytokines such as IL-1β, IL-6, TNF-α, and IL-12, which produce suppressor cytokines such as IL-10 and TGF-βe; an ability to suppress excessive activation of inflammatory NF-κB signaling cascade against the effect of inflammation inducing substances.

In the method for modifying an antigen presenting cell and the method for producing a regulatory dendritic cell of the present invention, examples of "cells" with which the fermented product of a cereal plant-derived material or a processed product thereof is brought into contact include antigen presenting cells such as dendritic cells, macrophages, and monocytes, and undifferentiated cells that can differentiate into antigen presenting cells (e.g., stem cells and precursor cells that can differentiate into dendritic cells, and particularly, bone-marrow-derived stem cells and peripheral blood mononuclear cells). Preferable cells are differentiation-induced cells obtained by stimulating bone-marrow-derived cells with a cytokine such as Flt-3L.

The present invention further relates to a method for producing regulatory T cells, which comprises a step of bringing the fermented product of a cereal plant-derived material or a processed product thereof of the into contact with cells collected from a subject.

As used herein, the term "regulatory T cell" (Treg) refers to a specific T cell subpopulation that suppresses immune reaction and maintains homeostasis and self tolerance. The regulatory T cell is defined differently depending on literatures and are not unambiguously defined; however, for example, the regulatory T cell has the characteristic that it constitutively expresses CD4, CD25, and FoxP3.

In the method for producing regulatory T cells of the present invention, examples of "cells" with which the fermented product of a cereal plant-derived material or a processed product thereof of the invention is brought into contact include naive T cells. The naive T cells can be obtained by further screening cells isolated from the spleen for expression of CD4 and CD62L, for example.

In the method for modifying antigen presenting cells, the method for producing regulatory dendritic cells, and the method for producing regulatory T cells of the present invention, the fermented product of a cereal plant-derived material or a processed product thereof of the invention to be brought into contact with an isolated cell is added in a concentration from 1 μg/mL to 500 μg/mL, preferably from 5 μg/mL to 250 μg/mL, more preferably from 10 μg/mL to 150 μg/mL, and particularly preferably from 25 μg/mL to 100 μg/mL, to an appropriate culture medium or an incubation solution, so as to bring the fermented product or processed product into contact with the isolated cell. The contact time is from 1 hour to 28 days, preferably from 12 hours to 14 days, more preferably from 1 to 12 days, and most preferably from 3 to 10 days.

The present invention also relates to the fermented product of a cereal plant-derived material or a processed product thereof of the present invention, which has an effect of modifying antigen presenting cells, and a composition for modification of antigen presenting cells, which comprises the fermented product of a cereal plant-derived material or a processed product thereof. Moreover, the present invention relates to the fermented product of a cereal plant-derived material or a processed product thereof, which has an effect of inducing regulatory T cells, and a composition for inducing regulatory T cells, which comprises the fermented product of a cereal plant-derived material or a processed product thereof. Furthermore, the present invention relates to a composition for inhibition of inflammatory T cell proliferation that is induced by an antigen associated with an autoimmune disease, allergy, or the like. The composition can comprise, in addition to the fermented product of a cereal plant-derived material or a processed product thereof of the present invention, the above-mentioned pharmaceutically acceptable excipient, or, an additive(s) (e.g., a buffer or a tonicity agent) that is generally used for reagents used in vitro.

As described later in the Examples, the present inventors have now isolated ergosta-5,7,14,22-tetraen-3β-ol, which is a compound represented by the following structural formula, from wheat bran fermented with a koji microorganism (in other sections herein, this compound is also referred to as "14-dehydroergosterol" or "14-DHE"). The present inventors have now further found for the first time that the thus purified 14-dehydroergosterol has the effect of suppressing the immune reaction that is mediated by DCs, as in the fermented product of a cereal plant-derived material or a processed product thereof of the present invention. Also, it is speculated based on the finding that 14-dehydroergosterol is an active ingredient responsible for the immunoregulatory effect of the fermented product of a cereal plant-derived material or a processed product thereof of the present invention. Chemical formula:

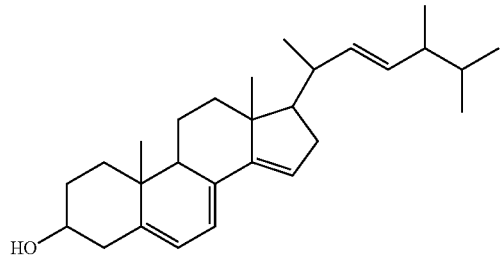 [SMILES: CC(C)C(C)/C=C/C(C)C1CC=C2C3=CC=C4CC(O)CCC4(C)C3CCC21C]

Therefore, the fermented product of a cereal plant-derived material or a processed product thereof of the present invention preferably contains 14-dehydroergosterol.

14-dehydroergosterol (14-DHE) was discovered in 1951 in *Aspergillus niger* (Barton, D H R., and Bruun, T., J. Chem. Soc., 2728-2733 (1951)) and re-discovered in 2009 as a component of kiwi fruit skin (Compound 8 in Fiorentino, A. et al., J. Agric. Food Chem., 57: 4148-4155 (2009)). However, its physiological activity has not yet been reported.

Specifically, the physiological activity of 14-dehydroergosterol has now been demonstrated by the present inventors that it is a substance effective for prevention or treatment of conditions associated with excessive activation of the immune system, such as immune diseases.

Thus, the present invention also relates to an immunomodulator or immunoregulatory foodstuff or beverage comprising 14-dehydroergosterol, and a pharmaceutical composition for prevention or treatment of immune diseases, which comprises 14-dehydroergosterol.

The dosage of 14-dehydroergosterol varies depending on various factors such as age, body weight, sex, and the degree of obesity of a subject; however, typically the dosage of 14-dehydroergosterol per day is 1 mg or more and preferably 5 mg or more. The interval of administration is not particularly limited.

The present invention further relates to a method for modifying antigen presenting cells or a method producing regulatory dendritic cells, which comprises a step of bringing 14-dehydroergosterol into contact with cells collected from a subject.

In the method for modifying antigen presenting cells and the method for producing regulatory dendritic cells of the present invention, examples of "cells" with which 14-dehydroergosterol is brought into contact include antigen presenting cells such as dendritic cells, macrophages, and monocytes, and undifferentiated cells that can differentiate into antigen presenting cells (e.g., stem cells and precursor cells that can differentiate into dendritic cells, and particularly, bone-marrow-derived stem cells and peripheral blood mononuclear cells). Preferable cells are differentiation-induced cells obtained by stimulating bone-marrow-derived cells with a cytokine such as Flt-3L.

In the method for modifying antigen presenting cells and the method for producing regulatory dendritic cells of the present invention, 14-dehydroergosterol to be brought into contact with the isolated cell is added in a concentration from 0.1 μM to 100 μM, preferably from 0.2 μM to 50 μM, more preferably from 0.5 μM to 25 μM, and particularly preferably from 1 μM to 10 μM, to an appropriate culture medium or an incubation solution, so as to bring the 14-dehydroergosterol into contact with the isolated cell. The contact time is from 1 hour to 28 days, preferably from 12 hours to 14 days, more preferably from 1 to 12 days, and most preferably from 3 to 10 days.

The present invention further relates to a method for producing regulatory T cells, which comprises a step of bringing 14-dehydroergosterol into contact with cells collected from a subject.

In the method for producing regulatory T cells of the present invention, examples of "cells" with which 14-dehydroergosterol is brought into contact are naive T cells. Naive T cells can be obtained by further screening cells isolated from the spleen for expression of CD4 and CD62L, for example.

In the method for producing regulatory T cells of the present invention, 14-dehydroergosterol to be brought into contact with isolated naive T cells is added in a concentration from 0.01 µM to 10 µM, preferably from 0.02 µM to 5 µM, more preferably from 0.05 µM to 2.5 µM, and particularly preferably from 0.05 µM to 1 µM, to an appropriate culture medium or an incubation solution, so as to bring 14-dehydroergosterol into contact with the isolated naive T cells. The contact time is from 1 hour to 28 days, preferably from 12 hours to 14 days, more preferably from 1 to 12 days, and most preferably from 3 to 10 days.

14-dehydroergosterol that is an active ingredient of the present invention is found in *Aspergillus niger* as described above. Hence, 14-dehydroergosterol may be contained in not only the fermented product of a cereal plant-derived material, but also fermented products of a broad range of koji microorganisms. Thus, the present invention relates to a koji microorganism-fermented product or a processed product thereof, which comprises 14-dehydroergosterol and has the effect of modifying antigen presenting cells, and to a composition comprising the koji microorganism-fermented product or a processed product thereof. Also, the present invention relates to a koji microorganism-fermented product or a processed product thereof, which comprises 14-dehydroergosterol and has an effect of modifying regulatory T cells, and to a composition comprising the koji microorganism-fermented product or a processed product thereof. The composition can comprise, in addition to the koji microorganism-fermented product or a processed product thereof of the present invention, the above-mentioned pharmaceutically acceptable excipient, or, an additive(s) (e.g., a buffer or a tonicity agent) that is generally used for reagents used in vitro.

As described herein, 14-dehydroergosterol has the effect of inducing regulatory T cells by modifying DCs, and the effect of inducing regulatory T cells by directly acting on naive T cells. Thus, the present invention also relates to a regulatory T cell-inducing agent comprising 14-dehydroergosterol.

Also, as described herein, 14-dehydroergosterol has the effect of suppressing inflammatory T cell proliferation resulting from antigen stimulation. Thus, the present invention also relates to an agent for suppressing inflammatory T cell proliferation, which comprises 14-dehydroergosterol.

The regulatory T cell-inducing agent or the agent for suppressing inflammatory T cell proliferation of the present invention can comprise, in addition to 14-dehydroergosterol as an active ingredient, the above-mentioned pharmaceutically acceptable excipient and the like.

The koji microorganism-fermented product or a processed product thereof and the composition comprising the same of the present invention have the effect of modifying antigen presenting cells. Thus, they can suppress immune reactions mediated by DCs, so that they are useful for prevention and treatment of immune diseases, for example.

Also, the koji microorganism-fermented product or a processed product thereof and the composition comprising the same of the present invention can induce regulatory T cells (Treg) from naive T cells, so that they are useful for prevention or treatment of immune diseases.

Furthermore, the koji microorganism-fermented product or a processed product thereof and the composition comprising the same of the present invention can suppress inflammatory T cell proliferation that is stimulated in vivo by various antigen sensitizations, and thus they are useful for prevention or treatment of immune diseases.

EXAMPLES

The present invention will be described in more details with reference to the following Examples, but the present invention should not be limited to the Examples.

Example 1

Preparation of Different Cereal Plant-Derived Materials Fermented with Koji Microorganisms and Processed Products Thereof Rice and barley products fermented with koji microorganisms were prepared as follows. Different commercial koji mold starters (yellow koji: Akita Konno Shoten, Japan, *Aspergillus oryzae* as a strong starter for fermentation; black koji: Akita Konno Shoten, Japan, black koji mild (*Aspergillus awamori*); red koji: Akita Konno Shoten, Japan (*Monascus anka*)) were separately inoculated at 0.1% by weight to steamed rice or steamed barley prepared based on the conventional method. Relative humidity was maintained at 80% or higher. Samples fermented with the yellow koji and samples fermented with the black koji were subjected to koji production at 35° C. for 72 hours, and samples fermented with the red koji were subjected to koji production at 30° C. for 7 days, while appropriately performing Japanese "teire" (which is a treatment for disintegrating aggregated koji).

Wheat bran and rice bran products fermented with koji microorganisms were prepared as follows. Demineralization water (550 mL) was added to 450 g of wheat bran (Nisshin Seifun Group Inc., Japan) or rice bran and then mixed well, followed by sterilization using an autoclave at 121° C. for 50 minutes. Different commercially available koji mold starters (black koji: Akita Konno Shoten, Japan, black koji mild (*Aspergillus awamori*); tempeh mold: Akita Konno Shoten, Japan (*Rhizopus oligosporus*)) were separately inoculated at 0.1% by weight to the thus sterilized raw materials. Relative humidity was maintained at 85% or higher and then culture was performed at 35° C. The "teire" was performed at the time points of 24 hours and 48 hours after the initiation of culture. Culture was completed at the time point of 72 hours.

Samples from koji-fermented products were lyophilized and then crushed using a household crushing apparatus. Forty (40) mL of 99.5% ethanol was added to 2 g each of the thus obtained lyophilized samples and then subjected to ultrasonication at 40° C. for 30 minutes with agitating, so that ethanol extraction was performed. The supernatant was filtered using filter paper, 40 mL of 99.5% ethanol was further added to the residue, so that extraction was similarly performed. The supernatant was similarly filtered using filter paper, and then the filtrates were mixed together. The thus obtained extract was concentrated using an evaporator and then further dried using a lyophilizer, followed by measuring the weight. After dissolution in 10 mL of 80% methanol, extraction with 10 mL hexane was performed 3 times, and the supernatants were taken together. The thus obtained hexane fraction and the remaining 80% methanol fraction were separately concentrated using an evaporator and then dried using a lyophilizer, followed by measuring each weight. The solidified hexane fraction was dissolved in 100% ethanol, and the solidified 80% methanol fraction was dissolved in an aqueous 50% ethanol solution. The resultants were used for various evaluations as stock solutions.

Each sample is shown in Table 1.

TABLE 1

|  | Hexane phase | Methanol phase |
| --- | --- | --- |
| Rice red koji | 1 | 11 |
| Barley black koji | 2 | 12 |
| Barley red koji | 3 | 13 |
| Forbidden rice black koji | 4 | 14 |
| Barley yellow koji | 5 | 15 |
| Rice yellow koji | 6 | 16 |
| Rice bran yellow koji | 7 | 17 |
| Wheat bran black koji | 8 | 18 |
| Rice bran black koji | 9 | 19 |
| Rice bran tempeh | 10 | 20 |

Example 2

Evaluation of Regulatory DC Induction Activity

To obtain substances having activity effective for alleviating, preventing, and treating graft rejection and various immune diseases including graft-versus-host disease, samples prepared in Example 1 were evaluated using as indicators: (A) decreases in the expression levels of cell surface maturation factors represented by CD86; (B) decreases in the expression levels of inflammatory cytokines such as IL-12 produced by DCs; and (C) increases in the expression levels of regulatory cytokines such as IL-10 produced by DCs, in response to inflammatory stimuli.

Effects of each sample on DC induction from mouse bone marrow cells and DC differentiation were evaluated by the method described below.

<Experimental Method>

Cereal plant-derived materials and the koji-fermented products thereof prepared in Example 1, as shown in Table 1, were tested. First, C57BL/6 mouse bone marrow cells were recovered from the thigh bone according to the conventional method and then subjected to removal of erythrocytes. Next, the thus obtained bone marrow cells were suspended in the RPMI medium (Gibco) containing 10% FCS and 2 μM β-mercaptoethanol at $1 \times 10^6$ cells/mL. Flt-3L (R&D systems), a DC-induced cytokine, was added at a final concentration of 100 ng/mL to the thus obtained cell suspension. Subsequently, each sample shown in Table 1 was added at a final concentration of 50 μg/mL. The cells were cultured in $CO_2$ incubator at 37° C. and 5% $CO_2$ for 1 week. At the time point of the last 24 hours of culture, LPS (Sigma-Aldrich Corporation) was added at a final concentration of 1 ng/mL. As a control, a sample to which no LPS had been added was prepared.

Cells were recovered on day 8 of culture and then evaluated by analysis of the above (A) CD86 expression level using a flow cytometer. In brief, cells were recovered, washed, and then stained with each antibody (anti-CD11c-APC, anti-CD11b-FITC, anti-B220-PerCP, and anti-CD86-PE (all available from Becton, Dickinson and Company)) for 30 minutes at 4° C. The cells were then washed and analyzed using an FACS Cantoll (Becton, Dickinson and Company).

Myeloid DC ("mDC") and plasmacytoid DC ("pDC") were generated with the culture of DCs using Flt-3L. In this Example, a gate was set on mDCs defined by $CD11c^+CD11b^+B220^-$ and then analysis was conducted.

The culture supernatant was subjected to ELISA for examining the above (B) IL-12 production amount and (C) IL-10 production amount. Measurement was performed using an OptEIA Mouse ELISA Set (Becton, Dickinson and Company) as an ELISA kit according to the manufacturer's instructions.

<Experimental Results>

(A) Effect of Each Sample on Expression of Maturation Marker CD86 in Response to LPS Stimulation FIG. 1 shows the results of assaying samples listed in Table 1. In the case of a control (in which ethanol, as a sample solvent, alone had been added), the CD86 expression level (evaluated based on mean fluorescence intensity: MFI) increased explosively in response to LPS stimulation. As a result of the addition of each sample, the phenomenon of suppressing the increase in the CD86 expression level was observed. In particular, samples 7, 8, 9, 10, and 20 caused the CD86 expression level to decrease to 50% or less of that of the control, and thus the significant decreases were observed.

Figure 2:
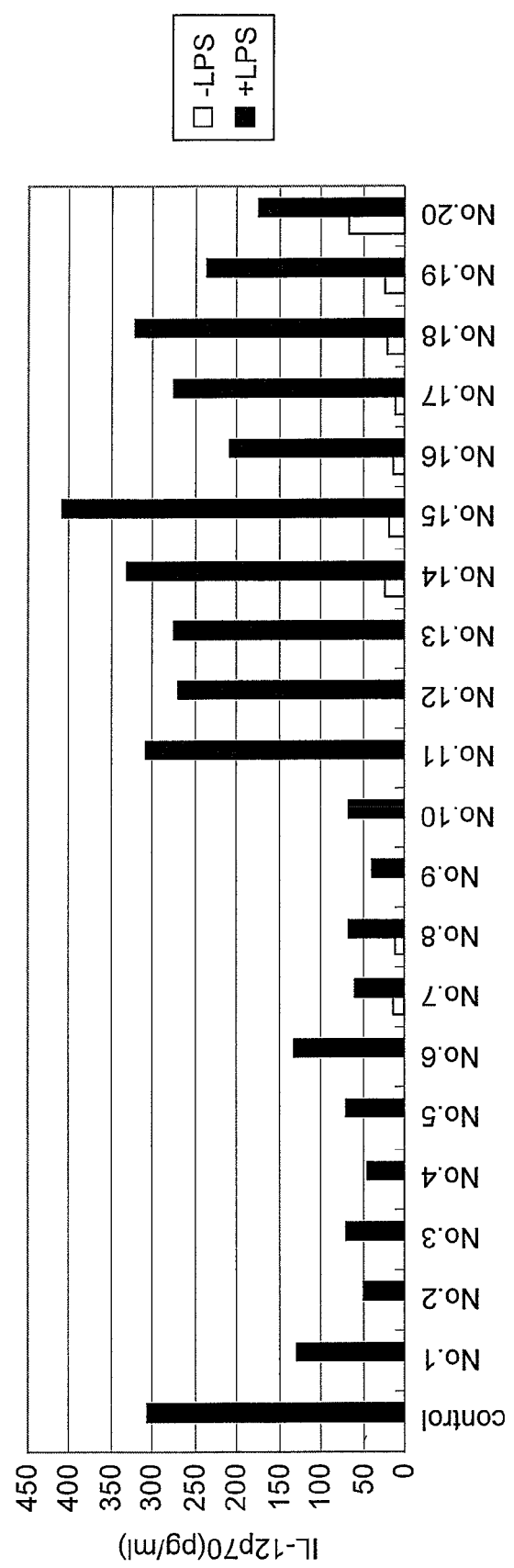
FIG. 2 is the graph showing the effects (i.e., IL-12p70 production) of different cereal plant-derived materials fermented with koji or processed products thereof on DC differentiation.

(B) Effect of Each Sample on Expression of Inflammatory Cytokine IL-12p70 in Response to LPS Stimulation FIG. 2 shows the results of assaying samples listed in Table 1. In all hexane-extracted fractions obtained by hexane extraction, from No. 1 to No. 10, significantly suppressed IL-12p70 expression was observed.

Figure 3:
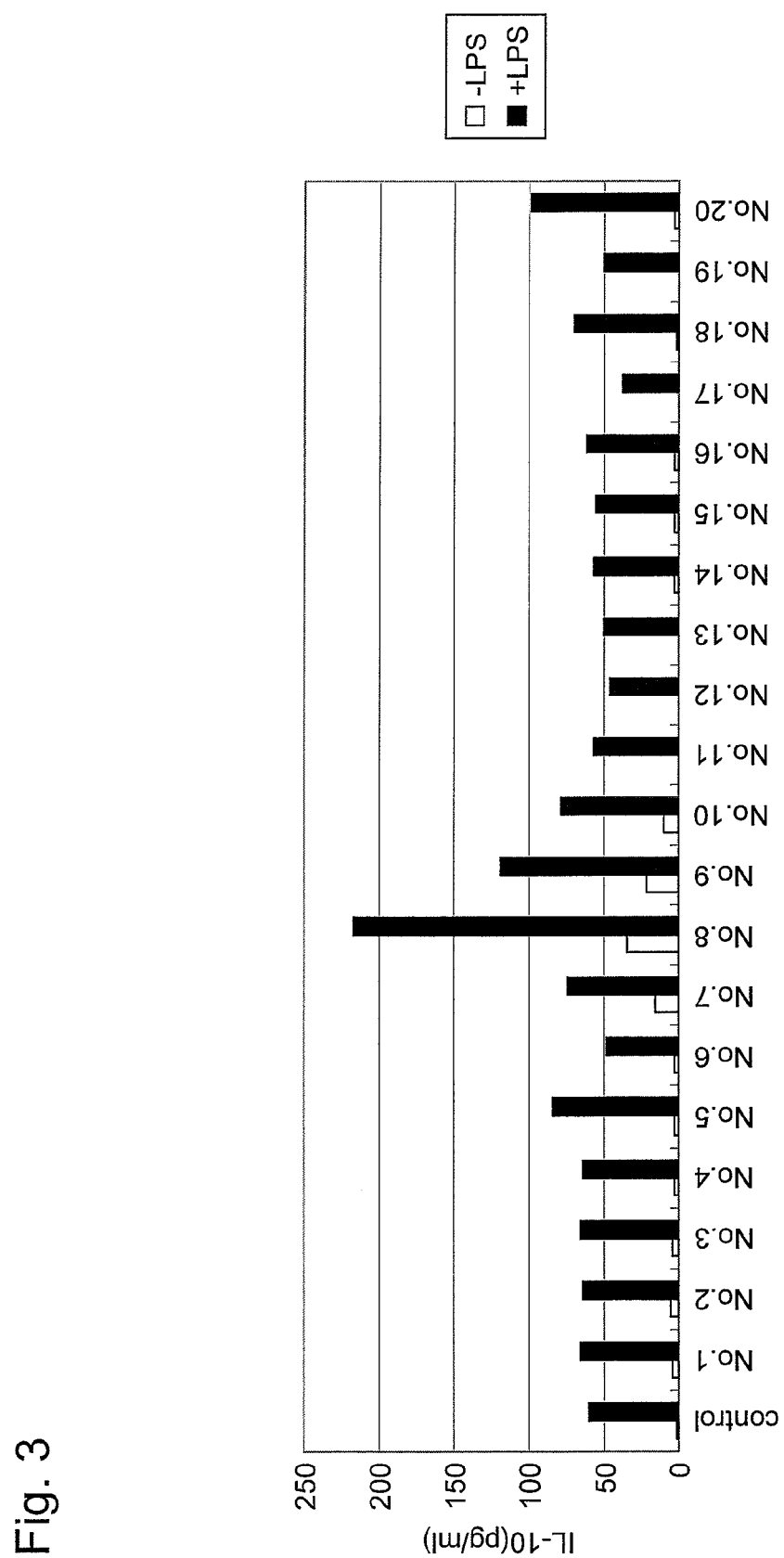
FIG. 3 is the graph showing the effects (i.e., IL-10 production) of different cereal plant-derived materials fermented with koji or processed products thereof on DC differentiation.

(C) Effect of Each Sample on Expression of Regulatory Cytokine IL-10 in Response to LPS Stimulation FIG. 3 shows the results of assaying samples listed in Table 1. Only in the case of No. 8, a significant activity to accelerate IL-10 expression was observed.

As a result, No. 8 sample, which was wheat bran that had been fermented with black koji and then subjected to ethanol extraction and hexane fractionation, was specified as the one that completely satisfied the conditions (A) to (C). It can be said that the No. 8 sample induces regulatory DC. Also, it was revealed that the No. 7, 9, 10, and 20 samples had anti-inflammatory activity since no effect of accelerating IL-10 production was observed, but the effect of inhibiting DC activation (i.e., decreased expression of the maturation marker (CD86) in response to LPS stimulation and decreased production of the inflammatory cytokine (IL-12)) were observed.

Example 3

Comparison Between Wheat Bran Fermented with Koji and Other Regulatory DC Inducing Agents An extract from wheat bran fermented with koji confirmed in Example 2 to have regulatory DC induction activity was compared with known representative regulatory DC-inducing agents.

It has been reported that adding rapamycin during DC induction causes differentiation of DCs exhibiting decreased CD86/MHCII expression levels and decreased IL-12p70 production (Journal of Immunology, 2007, 178: 7018-7031). Meanwhile, Sato et al. have reported that adding IL-10/TGF-β simultaneously with initiation of DC induction causes decrease in expression levels of a series of DC maturation markers (Immunity, 2003, 18: 367-379.). Also, it has been reported that γ-oryzanol contained in rice bran has an anti-inflammatory effect and thus improves enteritis, although its involvement in DCs remains unknown (Br J Pharmacol, 2008, 154: 812-824.). In this Example, whether the wheat bran fermented product has an effect equivalent to those of the agents was examined as described below.

<Experimental Method>

The hexane fraction (No. 8) (in Table 1) prepared in Example 1 from wheat bran fermented with koji was used for the test. Since GM-CSF is used as a DC-inducing agent in the above-mentioned reports concerning rapamycin and IL-10/ TGF-β, DCs were induced in each system of GM-CSF and Flt-3L and then each regulatory DC-inducing agent was evaluated.

(A) DC Induction System Using Flt-3L

In a manner similar to the experimental method in Example 2, bone marrow cells were prepared from C57BL/6 mouse thigh bone, the cells were suspended at $1 \times 10^6$ cells/mL in a medium, and then Flt-3L was added at 100 ng/mL. An extract from wheat bran fermented with koji, γ-oryzanol (Wako Pure Chemical Industries, Japan), or IL-10/TGF-β (produced by R&D systems and Peprotech, respectively) were added at 50 μg/mL for the former two or at 20 ng/mL for the latter two on day 0 after the initiation of culture. Rapamycin (Wako Pure Chemical Industries, Japan) was added at 10 ng/mL on day 3 after the initiation of culture. Culture was performed for 7 days and, at the time point of the last 24 hours of culture, LPS was added in a final concentration of 1 ng/mL.

Regarding an evaluation method, expression intensities of the cell-surface DC activation markers CD40, CD86 and MHCII and the suppression marker PD1L were evaluated by analysis using a flow cytometer. A gate was set on mDCs similarly to Example 1 and then analysis was conducted. Staining was performed using anti-CD11c-APC, anti-CD11b-APC-Cy7, anti-B220-PerCP, anti-CD40-FITC and anti-CD86-PE, or anti-CD11c-APC, anti-CD11b-APC-Cy7, anti-B220-PerCP, anti-MHCII-FITC, and anti-PD1L-PE (all available from Becton, Dickinson and Company) and then analysis was conducted.

(B) DC Induction System Using GM-CSF

In a manner similar to the experimental method in Example 1, bone marrow cells were prepared from C57BL/6 mouse thigh bone, the cells were suspended at a concentration of $2 \times 10^5$ cells/mL in a medium, and then 20 ng/ml GM-CSF (R&D systems) was added. The concentration and timing of the added test substance were similar to those in the above examples.

Regarding an evaluation method, expression intensities of the cell-surface DC activation markers CD40, CD86 and MHCII and the suppression marker PD1L were evaluated by analysis using a flow cytometer. In the case of the DC induction using GM-CSF, only mDC was generated. As in the case of Flt-3L, a gate was set on mDCs defined by $CD11c^+CD11b^+B220^-$ and then analysis was conducted.

<Experimental Results>

(A) Results in DC Induction System Using Flt-3L

Figure 4:
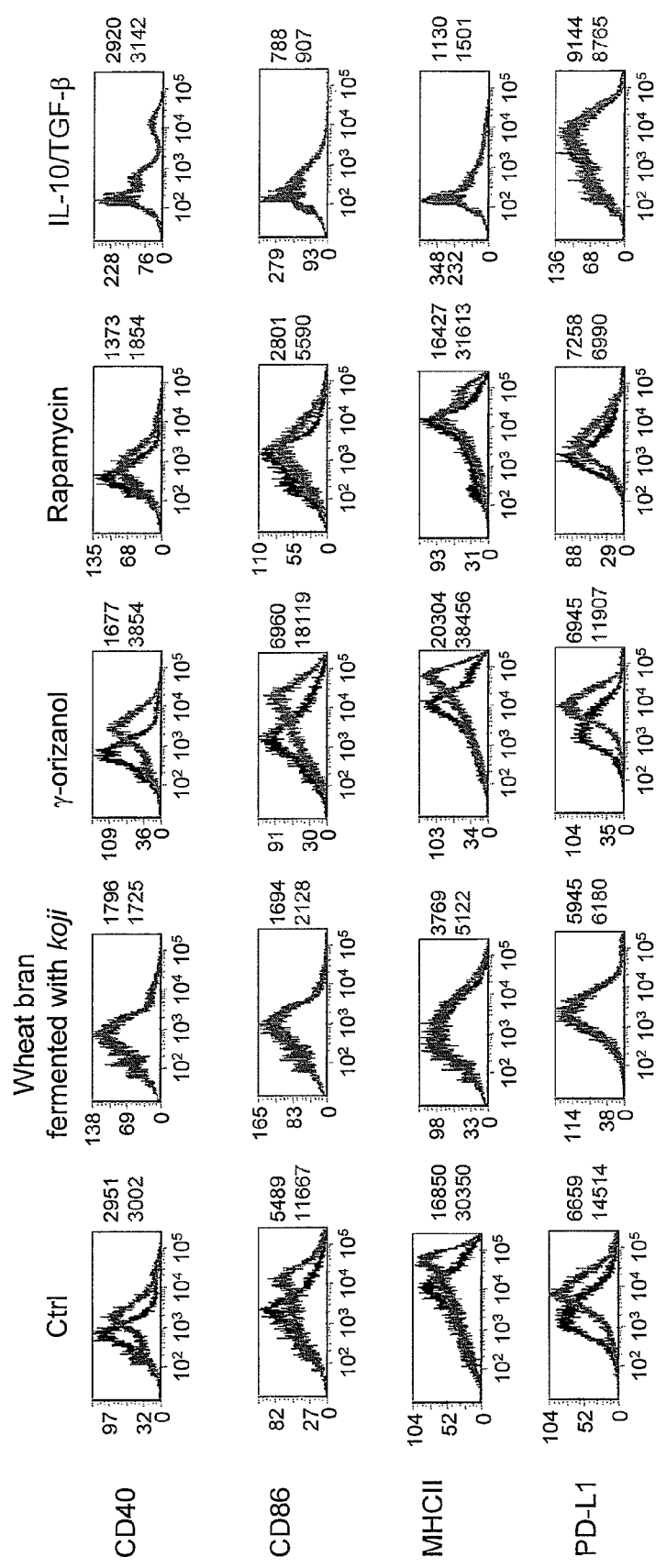
FIG. 4 shows the comparison of the effects of different immunosuppressors on DC differentiation based on Flt-3L.

First, in the case of addition of IL-10/TGF-β, DCs did not differentiate, and thus evaluation was impossible. As shown in FIG. 4, in the case of the extract from wheat bran fermented with koji (in FIG. 4, simply denoted as "fermented product of wheat bran," which also applies below), CD40, CD86 and MHCII reactions in response to LPS stimulation were significantly suppressed. On the other hand, in the case of γ-oryzanol, no fluctuation was observed for these activation markers, suggesting γ-oryzanol had no effect. In the case of rapamycin, slight suppression effects were observed for CD40 and CD86, but the effects were significantly inferior to those of the extract from wheat bran fermented with koji. In the case of the suppression marker PD1L on DCs, no significant fluctuations were observed in any samples.

(B) Results in DC Induction System Using GM-CSF

Figure 5:
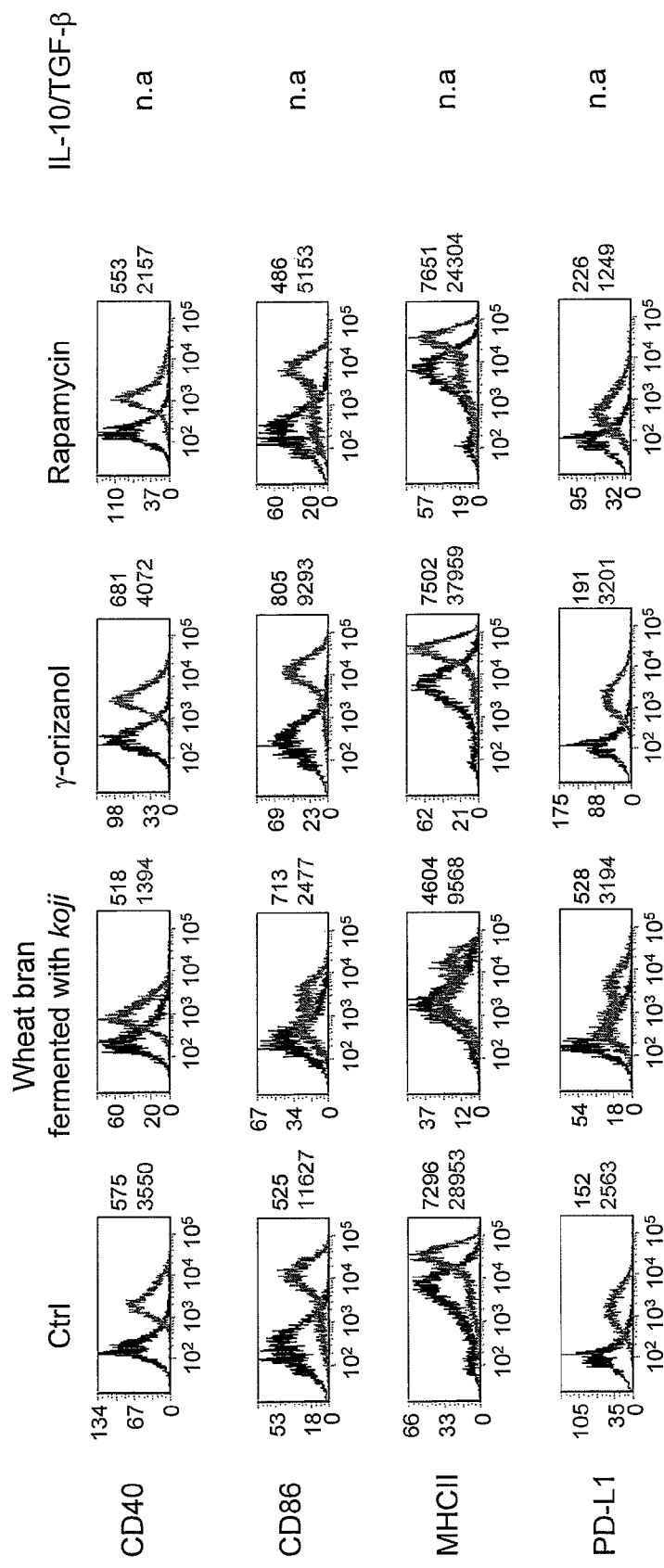
FIG. 5 shows the comparison of the effects of different immunosuppressors on DC differentiation based on GM-CSF.

As shown in FIG. 5, in the case of DCs treated with the extract from wheat bran fermented with koji, it was demonstrated that the expression of DC activation markers was suppressed to a degree stronger than that of the control even when no LPS had been added and, additionally, the DCs were almost unresponsive to LPS stimulation and were tolerant to inflammatory stimuli. In the case of γ-oryzanol, strong increases were observed in activation marker expression similarly to a control, and the effect of inducing regulatory DCs was not observed. In the case of rapamycin, regardless of addition or no addition of LPS, the effect of suppressing the expression of CD40 and CD86 was observed, but no such effect was observed for MHCII. Thus, limited generation of regulatory DCs was confirmed. In the case of IL-10/TGF-β, suppressed expression of CD40, CD86 and MHCII was observed as in the case of the extract from wheat bran fermented with koji. However, the decreased expression degree of CD11c (a DC differentiation marker) was observed, suggesting inhibition of DC differentiation itself.

Based on the above results, it was demonstrated that the food-derived extract from wheat bran fermented with koji, which is highly competitive in terms of safety, adverse effect and cost, can induce regulatory DCs with effectiveness equivalent to or higher than those of rapamycin and IL-10/ TGF-β, which are known regulatory DC-inducing agents.

Example 4

Evaluation of T Cell Proliferation-Supporting Capacity and Cytokine Production Capacity of DCs Treated with an Extract from Wheat Bran Fermented with Koji For evaluation of the T cell proliferation-supporting capacity of DCs treated with an extract from wheat bran fermented with koji, the mixed-lymphocyte reaction (MLR) test was conducted.

<Experimental Method>

Wheat bran fermented with koji (No. 8 in Table 1) prepared in Example 1 was used in the test. In a manner similar to that in the above examples, except for the use of a BALB/c mouse as a source of bone marrow cells, DCs were induced using Flt-3L in the presence of the extract from wheat bran fermented with koji, and then during the last 24 hours, stimulation was performed by treating with LPS. For a control, cells were prepared without adding the extract from wheat bran fermented with koji.

Subsequently, $CD11b^-CD11c^+B220^-$ mDCs were sorted using the cell sorter (FACS Aria). Next, DCs were treated with mitomycin C, so that they would stop their own proliferation during the culture period. In brief, the cells were incubated in the RPMI1640 medium containing 10 μg/mL mitomycin C (NACALAI TESQUE, Japan) at 37° C. for 30 minutes and then washed twice with RPMI medium.

Next, $CD3^+CD4^+CD62L^+$ naive $CD4^+$ T cells were sorted from C57BL/6 mice using a cell sorter, and then fluorescent-stained with a CFSE label. In brief, the cells were stained using anti-CD3-APC-Cy7, anti-CD4-APC, and anti-CD62L-PE. Naive $CD4^+$ T cells were sorted and then stained using the CellTrace CFSE Cell proliferation kit (Molecular Probes) according to the manufacturer's instructions.

Finally, BALB/c-derived DCs for which mitomycin treatment had been completed and C57BL/6-derived naive $CD4^+$ T cells were mixed at $DC:CD4^+T=1:10$ (the number of cells) and then cultured for 7 days. After completion of culture, the degrees of $CD4^+$ T cell division and proliferation were evaluated for decrease in CFSE intensity. Also, production of the inflammatory cytokines TNF-α and IL-17 from differentiated CD4⁺ T cells was determined by intracellular cytokine staining. In brief, after staining of cell surface markers using anti-CD3-APC and anti-CD4-PerCP (both available from Becton, Dickinson and Company), cell membrane permeabilization treatment was performed using a Cytofix/Cytoperm Fixation/Permeabilization kit (Becton, Dickinson and Company), and then cytokine staining was performed using anti-TNFα-FITC and anti-IL-17-PE (both available from Becton, Dickinson and Company).

<Experimental Results>

Figure 6:
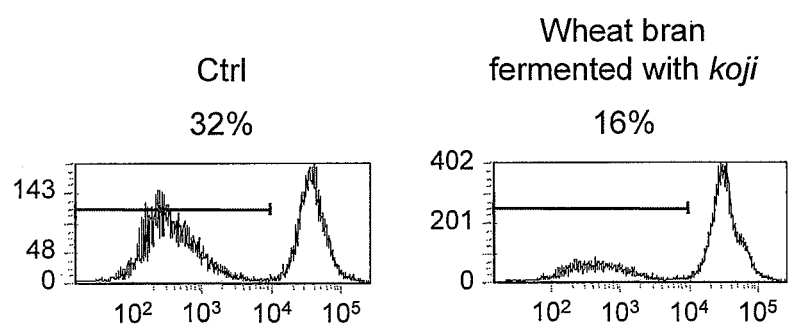
FIG. 6 shows changes in proliferation capacity of T cells stimulated by DCs treated with an extract from wheat bran fermented with koji.

(A) As shown in FIG. 6, it was demonstrated that DCs treated with an extract from wheat bran fermented with koji significantly decreased the division and proliferation-supporting capacity of CD4⁺ T cells, compared with the control, suggesting that the DCs treated with the extract had an anti-inflammatory effect to prevent acute T cell proliferation.

Figure 7:
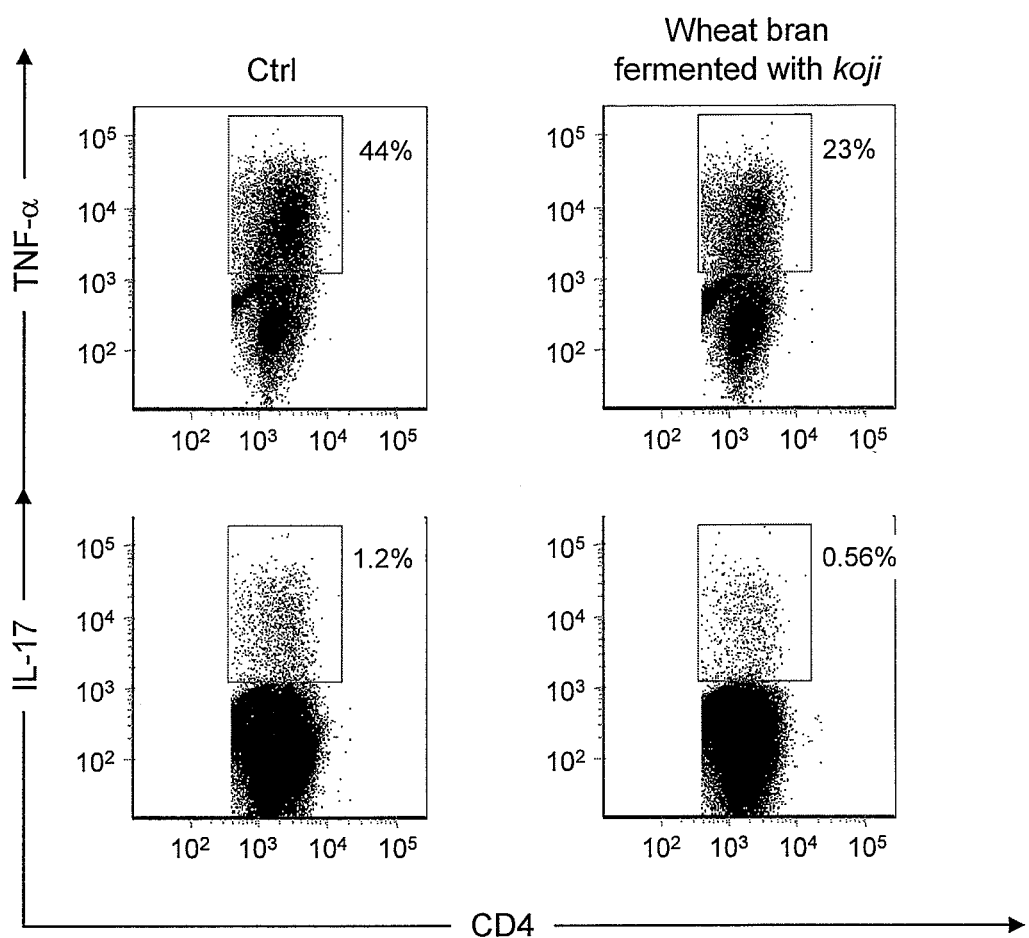
FIG. 7 shows changes in cytokine production of $CD4^+$ T cells induced by DCs treated with an extract from wheat bran fermented with koji.

(B) As shown in FIG. 7, the percentage of T cells positive for inflammatory cytokines, TNF-α and IL-17, in all T cells co-cultured with DCs treated with the extract from wheat bran fermented with koji was found to decrease to a half of that of the control DCs. The anti-inflammatory effect of the extract from wheat bran fermented with koji was thus also demonstrated.

Example 5

Evaluation of Regulatory T Cell (Treg)-Inducing Capacity of DCs Treated with an Extract from Wheat Bran Fermented with Koji DCs treated with the extract from wheat bran fermented with koji were assayed for evaluation of the capacity to induce conversion from naive T cells to Treg.

<Experimental Method>

(A) Examination of Antigen-Non-Specific Treg-Inducing Capacity

In a manner similar to that in the above Examples, DCs were induced using Flt-3L from BALB/c mouse bone marrow cells in the presence of a processed product of wheat bran fermented with koji and then treated with LPS for 24 hours. mDCs were sorted from the thus obtained cells in a manner similar to that in Example 3 and then subjected to mitomycin C treatment to stop the DC proliferation.

Next, naive CD4⁺ T cells were sorted from C57BL/6, DCs and the sorted cells were mixed at DC:CD4⁺T=1:10 (the number of cells), and then they were co-cultured. At this time, the medium was supplemented with 0.5 ng/mL TGF-β1 (Peprotech).

Seven days layer, cells were recovered and then the proportion of FoxP3⁺CD25⁺ T cells in CD⁺ T cells was determined using a flow cytometer (after staining of cell surface markers using anti-CD25-FITC, anti-CD3-APC-Cy7, and anti-CD4-PerCP, cell permeabilization treatment was performed using a Foxp3 Staining Buffer Set (e Bioscience) according to the manufacturer's instructions, and then intracellular Foxp3 was stained with anti-Foxp3-PE (e Bioscience)). As the control, mDCs prepared in the absence of the extract from wheat bran fermented with koji (no addition) and DCreg induced by adding IL-10/TGF-β to GM-CSF according to the method of Sato et al., were used.

(B) Examination of Antigen-Specific Treg-Inducing Capacity

Various DCs were prepared similarly to (A). Next, naive CD4⁺ T cells were sorted from DO11.10 mice (Charles River) having OVA-specific TCR, DCs were mixed with the sorted cells at DC:CD4⁺ T=1:10 (the number of cells), and then the cells were co-cultured. At this time, the medium was supplemented with 0.5 ng/mL TGF-β1 and 0.1 μM OVA323-339 peptide and then culture was performed for 5 days. Subsequently, Treg generation efficiency was determined as in (A) above.

<Experimental Results>

(A) Antigen-Non-Specific Treg-Inducing Capacity

Figure 8:
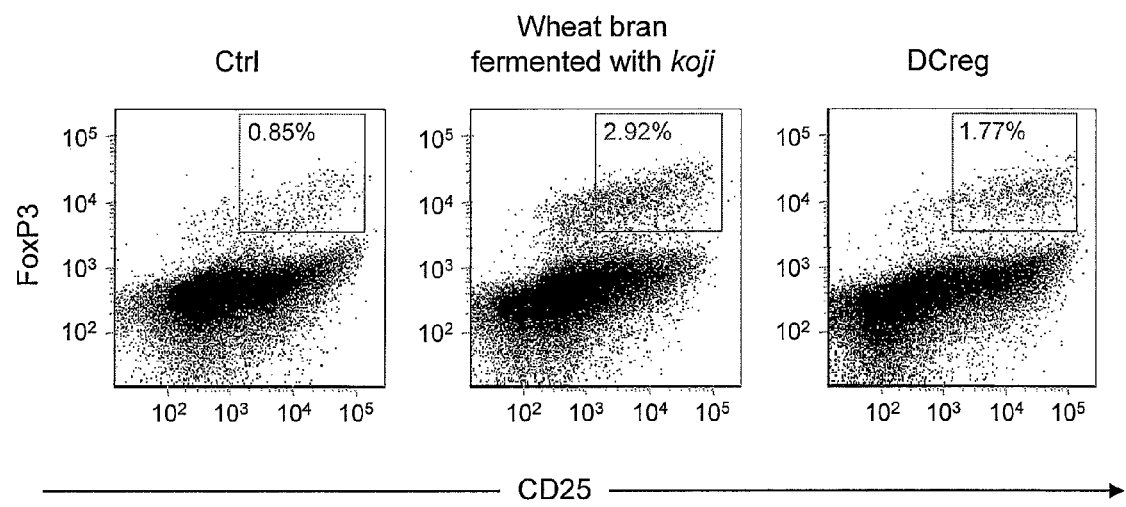
FIG. 8 shows the proportion of Treg induced by DCs treated with an extract from wheat bran fermented with koji (antigen non-specific reaction).

As shown in FIG. 8, Treg generation increased 3 times or more compared with the control after co-culture with DCs treated with the extract from wheat bran fermented with koji. On the other hand, DCreg generation was observed to increase 2 times or more compared with the control.

(B) Antigen-Specific Treg-Inducing Capacity

Figure 9:
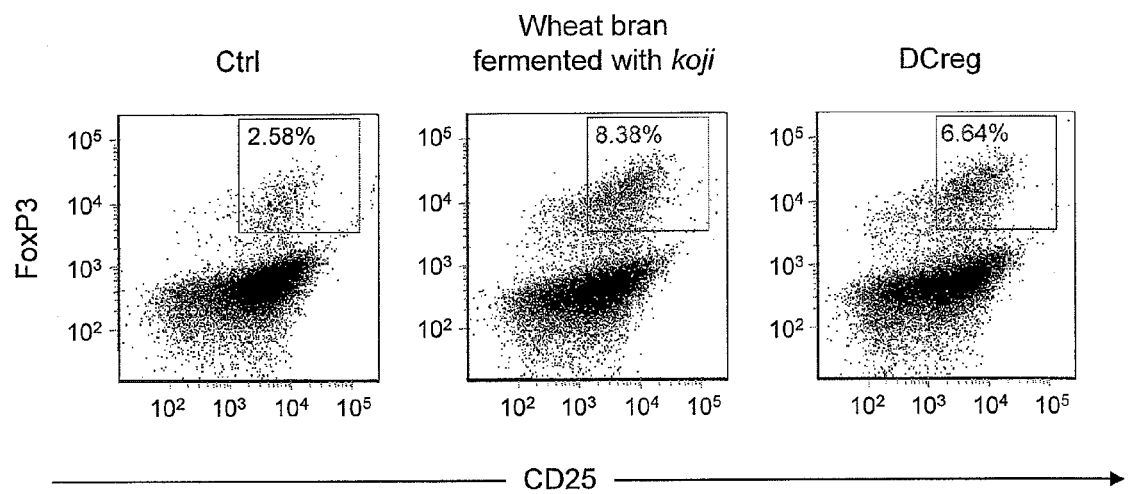
FIG. 9 shows the proportion of Treg induced by DCs treated with an extract from wheat bran fermented with koji (antigen specific reaction).

As shown in FIG. 9, Treg generation increased 3 times or more compared with the control after co-culture with DCs treated with the extract from wheat bran fermented with koji. On the other hand, DCreg generation was observed to increase 2 times or more compared with the control.

Based on the above results, it was demonstrated that DCs treated with the extract from wheat bran fermented with koji had the ability to efficiently induce Treg, and the effect was greater than that with DCreg prepared by the known method. This suggests that various immune diseases can be prevented and treated with the wheat bran fermented with koji through mediation of regulatory DC induction and the resulting increase in Treg.

Example 6

Comparison of Koji Mold Species Used

Whether or not the efficiency of regulatory DC induction differs depending on the types of koji mold species used for wheat bran fermentation was examined by comparing it among different koji mold species.

<Preparation of Samples>

Fermented products and extracts were prepared in a manner similar to that used in the method for preparing wheat bran fermented with black koji and processed products thereof as described in Example 1, except for the use of black koji (Akita Konno Shoten, Japan: black koji mild (*Aspergillus awamori*); Akita Konno Shoten, Japan: white koji for distilled spirits (*Aspergillus kawachii*); Higuchi Moyashi (Higuchi Matsunosuke Shouten, Japan: Higuchi black koji (*Aspergillus awamori*)), koji mold for shoyu (soy sauce) (Akita Konno Shoten, Japan: Shoyu (soy sauce) No. 1 (*Aspergillus sojae*)), yellow koji (Akita Konno Shoten, Japan: *Aspergillus oryzae* as a strong starter for fermentation), and a tempeh mold (Akita Konno Shoten, Japan: *Rhizopus oligosporus*) as commercial mold starters. Also, as samples that had not experienced fermentation, samples sterilized by the same method, to which no mold starter had been inoculated, were used.

<Experimental Method>

In a manner similar to that in Examples above, Flt-3L was added to C57BL/6 mouse bone marrow cells, so as to induce their differentiation into DCs, and at the same time, extracts from wheat bran fermented with koji (various koji mold species) were each added at a concentration of 50 μg/mL, and then culture was performed for 7 days. During the last 24 hours, the cells were stimulated with LPS, and then the concentrations of the cell activation markers CD86 and MHCII and the concentration of IL-10 in culture supernatants were measured.

<Experimental Results>

Figure 10:
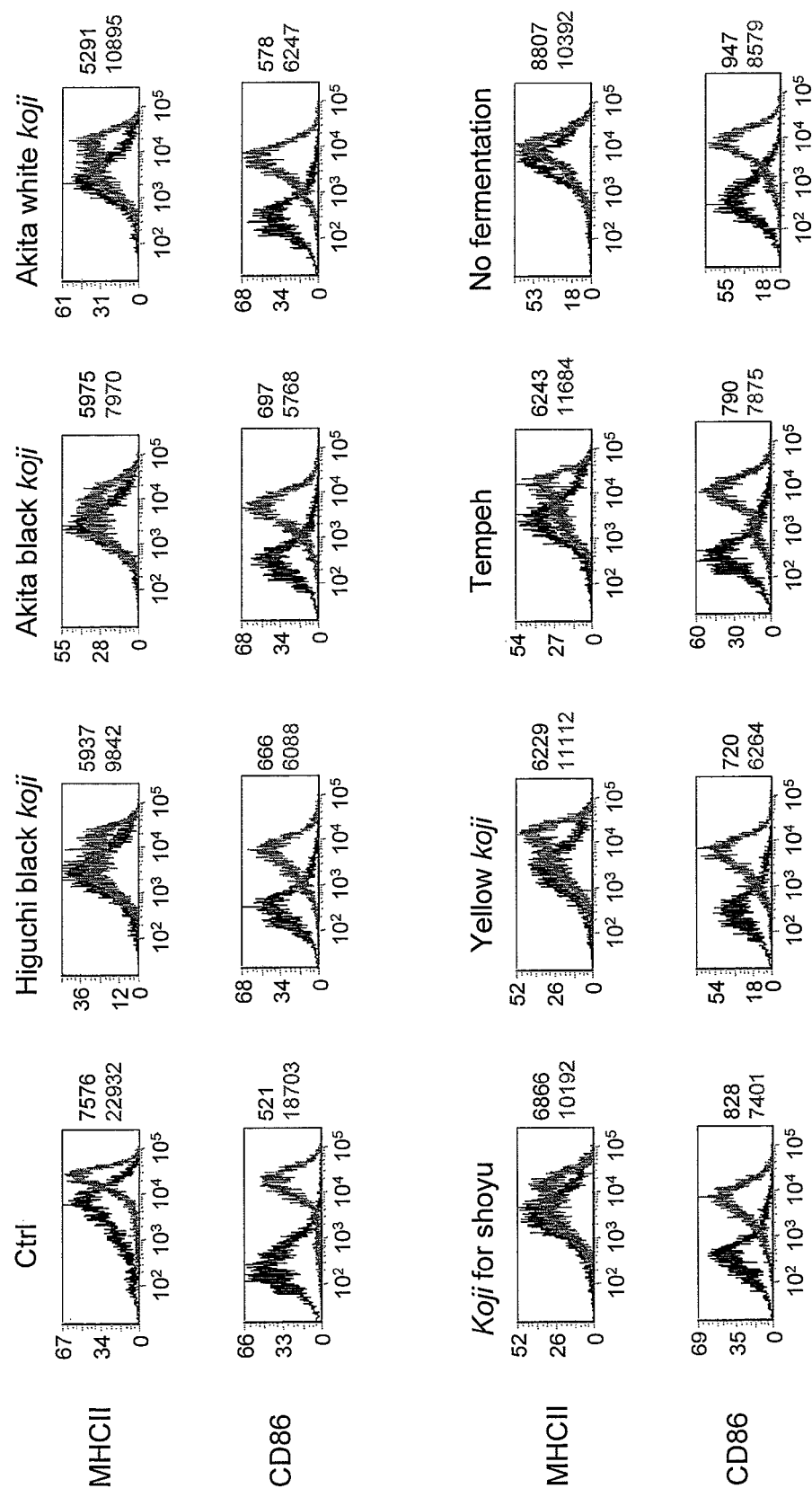
FIG. 10 shows the comparison of efficiencies of regulatory DC induction among *Aspergillus* species used for fermentation of wheat bran (cell surface markers).

As shown in FIG. 10, there were almost no significant differences in terms of CD86-suppressing activity, regardless of the types of strains used herein. Also, CD86-suppressing activity was observed for un-fermented products, although such results were slightly inferior to the other results. Black koji exhibited MHCII-suppressing activity at a level slightly higher than the levels of the other results.

Figure 11:
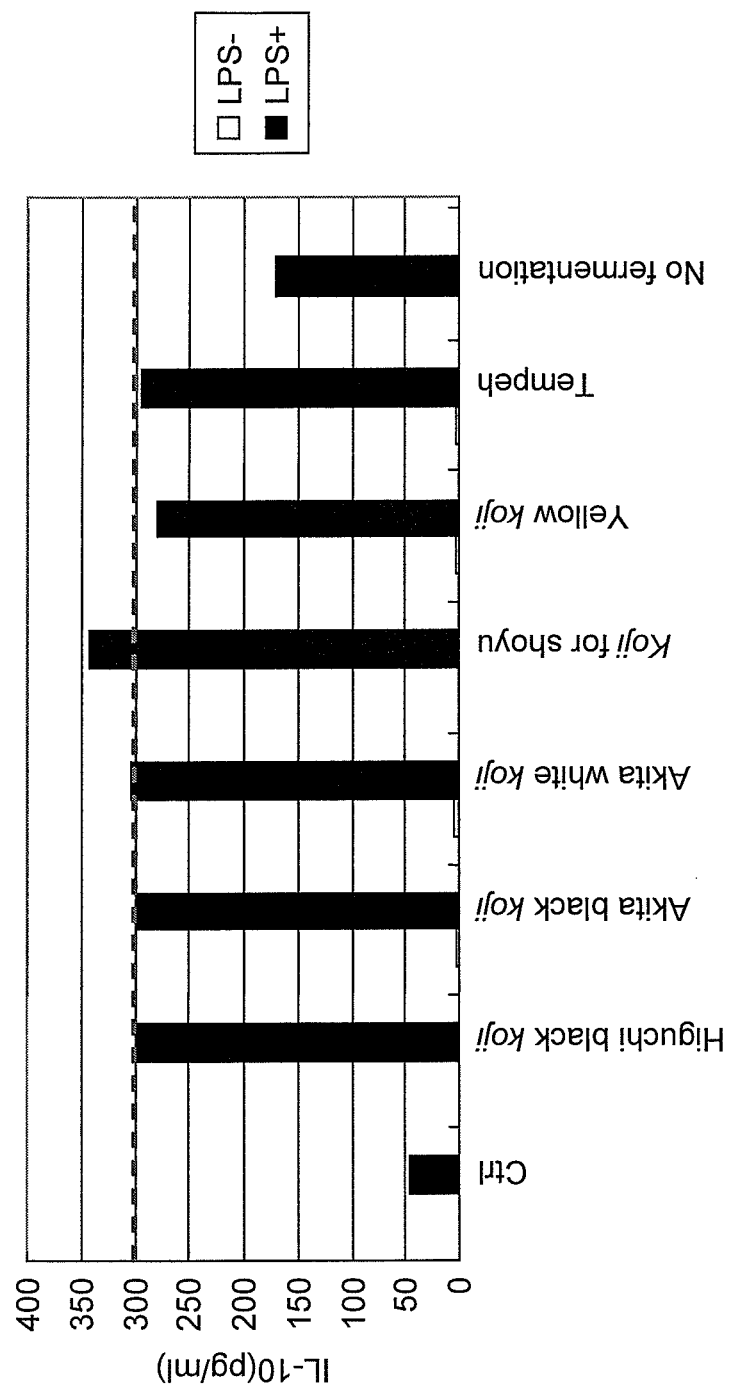
FIG. 11 shows the comparison of efficiencies of regulatory DC induction among *Aspergillus* species used for fermentation of wheat bran (IL-10 producing capacity).

FIG. 11 shows the concentration of IL-10. Stable IL-10 production was observed for every types of strains used, indicating that there was no difference among the used strains. Even in the case of the un-fermented product, IL-10-accelerating activity was observed to a degree that was about a half that of each of the other results.

Based on the above results, it was demonstrated that the black koji mold is preferable as a strain overall, and that the wheat bran itself as a raw material has a regulatory DC-inducing activity, and that such activity can be enhanced by fermentation.

Example 7

Relation Between Fermentation Conditions and Activity

Figure 12:
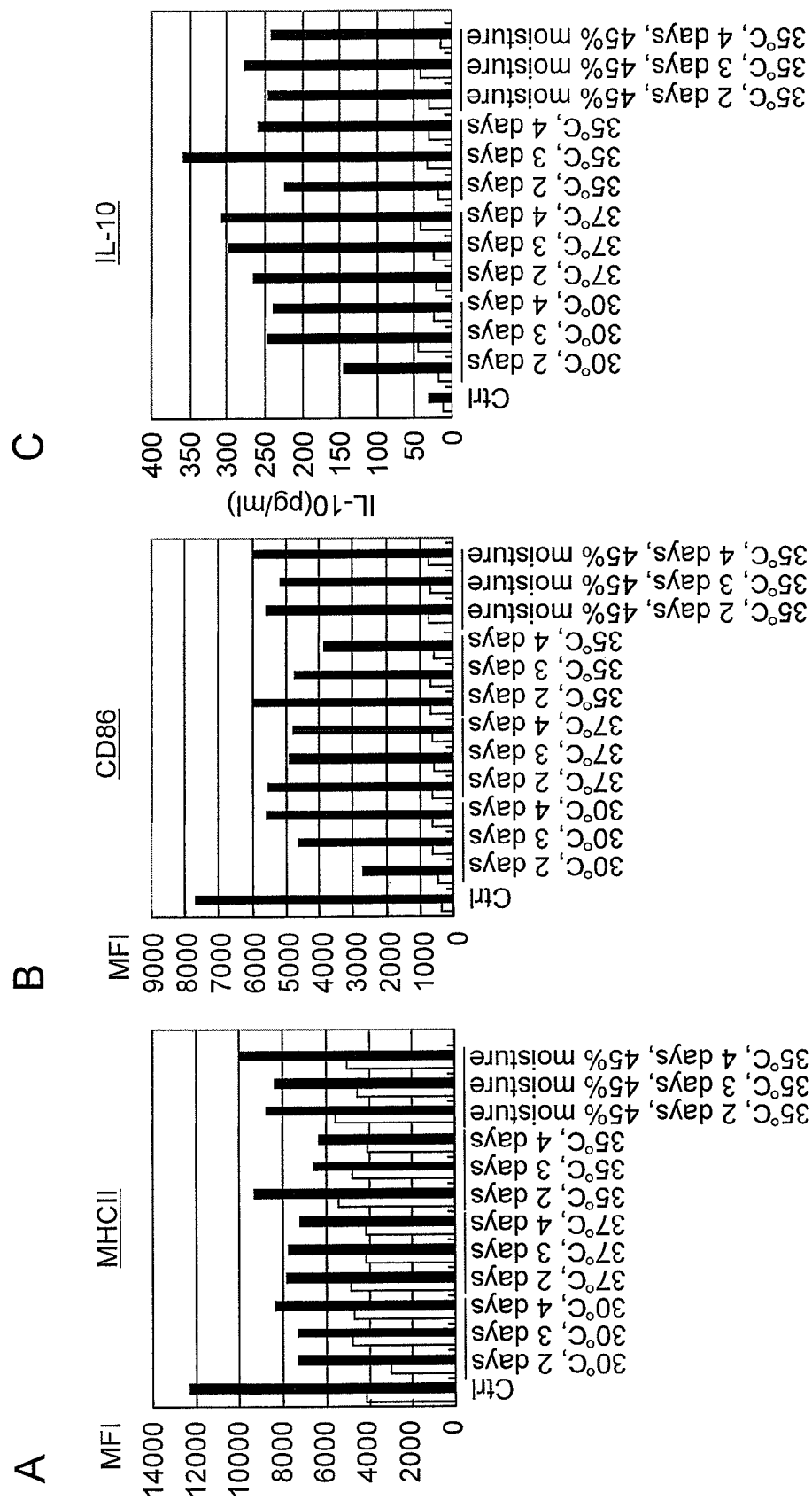
FIG. 12A is the graph showing the effects of conditions for fermentation of wheat bran with koji on DC maturation and/or differentiation (MHCII).
FIG. 12B is the graph showing the effects of conditions for fermentation of wheat bran with koji on DC maturation and/or differentiation (CD86).
FIG. 12C is the graph showing the effects of conditions for fermentation of wheat bran with koji on DC maturation and/or differentiation (IL-10).

Affection of temperatures, culture time (days), and moisture conditions upon fermentation of wheat bran with black koji on the advantageous effect of fermented products was examined.
<Preparation of Samples>
Fermented products and extracts were prepared in a manner similar to the preparation method for wheat bran fermented with black koji as described in Example 1 using Higuchi black koji (Higuchi Matsunosuke Shouten, Japan) as a commercial mold starter. The culture temperature was 30° C., 35° C., or 37° C. The culture time was 2, 3, or 4 days. The moisture was 55% of the basal condition, and 45%.
<Experimental Method>
In a manner similar to that in Examples above, Flt-3L was added to C57BL/6 mouse bone marrow cells so as to induce their differentiation into DCs, and at the same time, extracts from wheat bran fermented with koji under different culture conditions were each added at a concentration of 50 μg/mL, and then culture was performed for 7 days. During the final 24 hours, the cells were stimulated with LPS and then the concentrations of cell activation markers CD86 and MHCII and the concentration of IL-10 in culture supernatants were measured.
<Experimental Results>
As shown in FIG. 12, the degree of induction of IL-10 production was found to decrease slightly with 2-days culture at 30° C., and no particularly significant differences in the effect were found under other conditions.

Based on the above results, it was suggested that a substance having the stable activity was produced by fermenting wheat bran especially for 3 days or more at 30° C.

Example 8

Isolation of an Active Ingredient

A compound thought to be an active ingredient that exhibits an immunoregulatory effect as in the above Examples was isolated from wheat bran fermented with koji.
<Experimental Method>
Wheat bran fermented with koji was prepared by a method similar to that in Example 1 using the black koji (Akita Konno Shoten, Japan: black koji mild (*Aspergillus awamori*)) under the conditions of temperature 30° C., culture time 3 days, and moisture 55%. The thus obtained fermented product was further subjected to ethanol extraction and then hexane extraction, so that hexane extract was prepared. Three (3) g of the extract was obtained from 100 g of the lyophilized fermented product.

The thus obtained extract was dissolved in hexane at a concentration of 200 mg/mL. Three (3) mL of the resultant solution was applied to the column of Mega Bond Elute SI (20 g) (Varian) previously conditioned with hexane. Subsequently, the column was washed with 60 mL hexane and then eluted with 60 mL ethyl acetate, thereby recovering a substance adsorbed to the column. The thus obtained eluate was solidified to dryness using an evaporator. The substance adsorbed to the SI column (2.8 g) was obtained from 3 g of the hexane extract.

The obtained substance adsorbed to the SI column was dissolved in hexane/ethanol (80/20; v/v) to 200 mg/mL. Then the solution was subjected to high performance liquid chromatography (hexane/isopropanol=98/2) using UK-Slica (10×250 mm) (Imtakt Corp.). A fraction was fractionated with the retention time from 18 minutes to 19 minutes, and then evaporated to dryness. The residue was further dissolved in hexane/ethanol (20/80; v/v) and then the solution was subjected to high performance liquid chromatography (acetonitrile/isopropanol=99/1) using Develosil C30-UG-5 (10×250 mm) (Nomura Chemical Co., Ltd., Japan), so that a fraction was fractionated with the retention time from 32.5 to 33.5 minutes. The compound contained in the fraction was further analyzed by the conventional method, so that 14-dehydroergosterol, which has the following structural formula and physicochemical properties, was detected.
Chemical formula:

(1) Molecular weight: 394.32275 (the value determined by the high resolution APCI-Orbitrap method: m/z 395.33057 $(M+H)^{+)}$ (2) Molecular formula: $C_{28}H_{42}O$ (the calculated molecular weight: 394.323565)

(3) Solubility in solvent: insoluble in water, hardly soluble in ethanol, readily soluble in chloroform (4) Ultraviolet absorption spectrum (MeCN): 391 nm (5) $^1$H-NMR (CD$_3$OD) ppm: 6.15 (1H, m), 5.75 (1H, m), 5.65 (1H, dd, J=2.2, 5.9 Hz), 5.27 (1H, dd, J=7.0, 15.1 Hz), 5.21 (1H, dd, J=7.9, 15.1 Hz), 3.64 (1H, m), 2.51 (1H, ddd, J=2.2, 5.1, 10.6 Hz), 2.30 (1H, m), 2.20 (1H, m), 2.20 (1H, dd, J=3.2, 7.8 Hz), 2.06 (1H, m), 2.05 (1H, m), 1.94 (1H, m), 1.90 (1H, m), 1.87 (2H, m), 1.87 (1H, ddd, J=3.2, 7.0, 7.3 Hz), 1.71 (1H, m), 1.59 (1H, m), 1.57 (1H, m), 1.45 (1H, m), 1.45 (1H, ddd, J=3.2, 6.3, 6.5 Hz), 1.30 (1H, m), 1.05 (3H, d, J=6.8 Hz), 0.93 (3H, d, J=7.3 Hz), 0.92 (3H, s,), 0.89 (3H, s), 0.85 (3H, d, J=6.5 Hz), 0.83 (3H, d, J=6.3 Hz). (6) $^{13}$C-NMR(CD$_3$OD) ppm: 149.2 (s), 143.0 (s), 135.4 (s), 132.2 (s), 132.0 (s), 120.5 (s), 120.4 (s), 117.4 (s), 70.4 (s), 58.1 (s), 46.3 (s), 45.4 (s), 42.8 (s), 41.0 (s), 39.0 (s), 38.9 (s), 37.8 (s), 37.0 (s), 36.0 (s), 33.1 (s), 32.0 (s), 21.1 (s), 19.9 (s), 19.7 (s), 19.6 (s), 17.6 (s), 16.8 (s), 14.5 (s).

Example 9

Regulatory-DC-Inducing Activity of 14-Dehydroergosterol

Regulatory DC induction activity was evaluated for 14-dehydroergosterol (14-DHE) isolated and purified from wheat bran fermented with koji as described above and subjected to structural determination. As controls, ergosterol (Wako Pure Chemical Industries, Japan) and 9(11)-dehydroergosterol (9(11)-DHE) (Sigma-Aldrich Corp.), which are ergosterol-related substances, were used. Also, as conjugated linoleic acid (CLA) that was reported in connection with the inhibition of DC activation in the past, CLA (9Z, 11E) and CLA (10E, 12Z) (both, Cayman Chemical), and linoleic acid (Wako Pure Chemical Industries, Japan) were also subjected to activity determination (J. Immunol., 175(8): 4990-8, Oct. 15, 2005). As negative controls, a sample (none) to which no compound had been administered and a sample (ctrl) to which only LPS had been administered were also subjected to activity determination.

<Experimental Method>

In a manner similar to Example 2, bone marrow cells were prepared from C57BL/6 mouse thigh bone, and then dendritic cells were induced using Flt-3L. Each test substance was added simultaneously with the initiation of culture at a concentration of 1 μM, 5 μM, or 10 μM. Seven days later, LPS (from *Salmonella typhosa*) (Sigma-Aldrich Corp.) was added at 5 ng/mL and then 24 hours later the cells were recovered. Subsequently, the cells were stained for the following cell markers and then subjected to flow cytometry analysis. All antibodies used were produced by Becton, Dickinson and Company. $CD11c^+CD11b^+$ was set as a gate for mDCs and then the expression levels of CD40, CD80, CD86, I-A/I-E, and ICOS-L were measured. Also, IL-12p40 and IL-10 in culture supernatants were measured by ELISA.

<Results>

Figure 13:
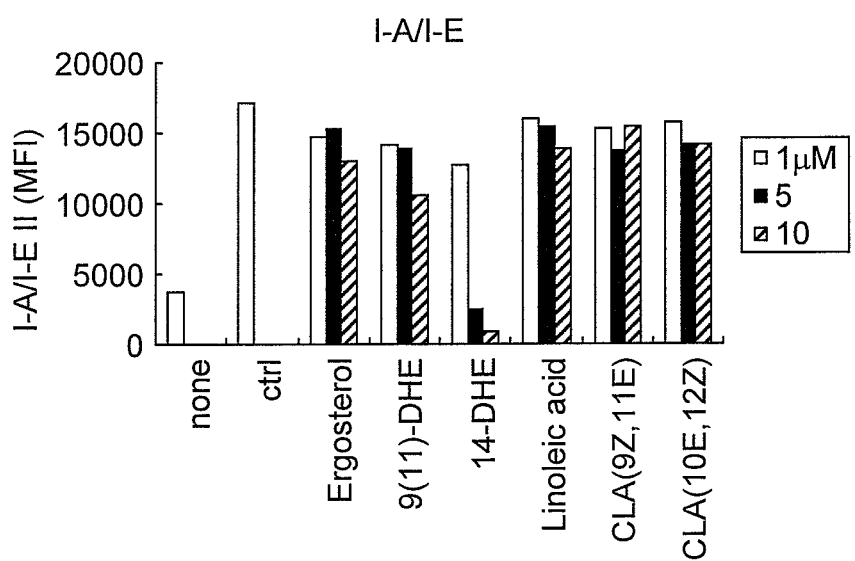
FIG. 13A is the graph showing the effects of 14-dehydroergosterol (14-DHE) and different control substances on DC maturation and/or differentiation (CD40).
FIG. 13B is the graph showing the effects of 14-DHE and different control substances on DC maturation and/or differentiation (CD80).
FIG. 13C is the graph showing the effects of 14-DHE and different control substances on DC maturation and/or differentiation (CD86).
FIG. 13D is the graph showing the effects of 14-DHE and different control substances on DC maturation and/or differentiation (I-A/I-E).
FIG. 13E is the graph showing the effects of 14-DHE and different control substances on DC maturation and/or differentiation (ICOS-L).
Figure 13:
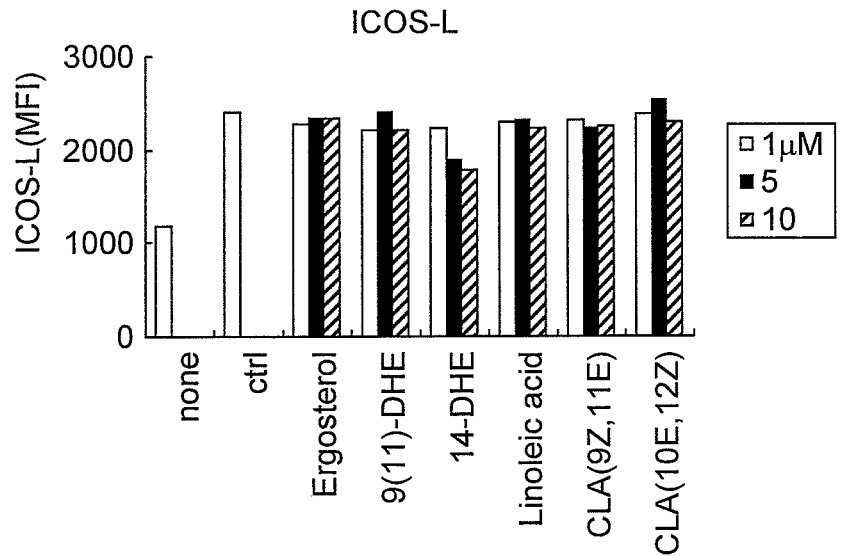

As shown in FIG. 13, the expression levels of the MHC class II molecule I-A/I-E and the costimulatory molecules CD40, CD80 and CD86, significantly decreased due to 14-DHE. Among control substances, the addition of 9(11)-DHE at the maximum concentration (10 μM) resulted in slight decrease observed in the expression levels of these molecules. These results demonstrated that 14-DHE found from the cereal plant-derived material of the present invention had extremely high activity of inducing unresponsiveness to inflammatory stimuli including LPS. It was also suggested that the position of a double bond in dehydroergosterol plays an important role in such activity.

The expression level of an ICOS-L marker serving as an indicator of the immunodepressive effect of DCs remained almost unchanged by 14-DHE. As a result, the ratio of the immune activation marker to the immunosuppression marker on DCs drastically leaned toward the suppression side with the addition of 14-DHE.

Figure 14:
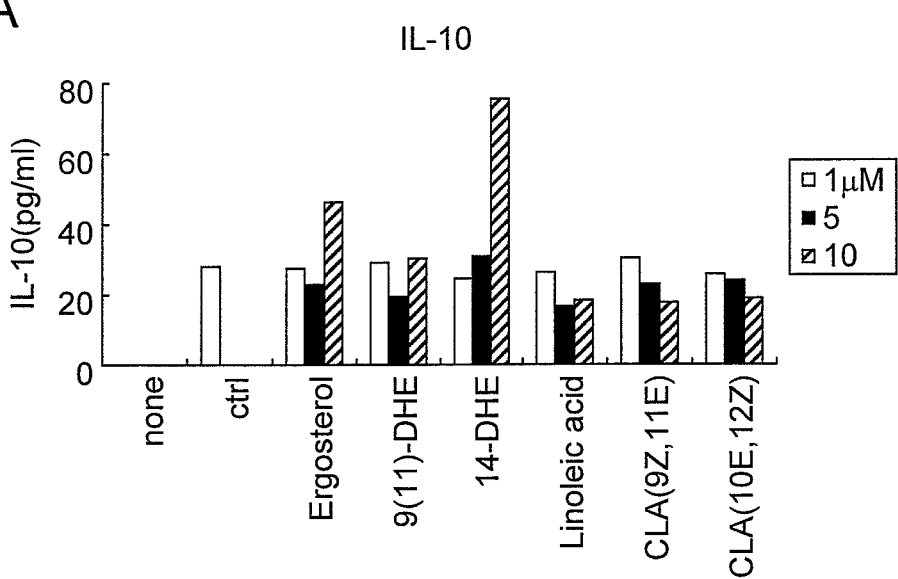
FIG. 14A is the graph showing cytokine production (IL-10) from DC treated with 14-DHE or different control substances.
FIG. 14B is the graph showing cytokine production (IL-12p40) from DCs treated with 14-DHE or different control substances.
Figure 14:
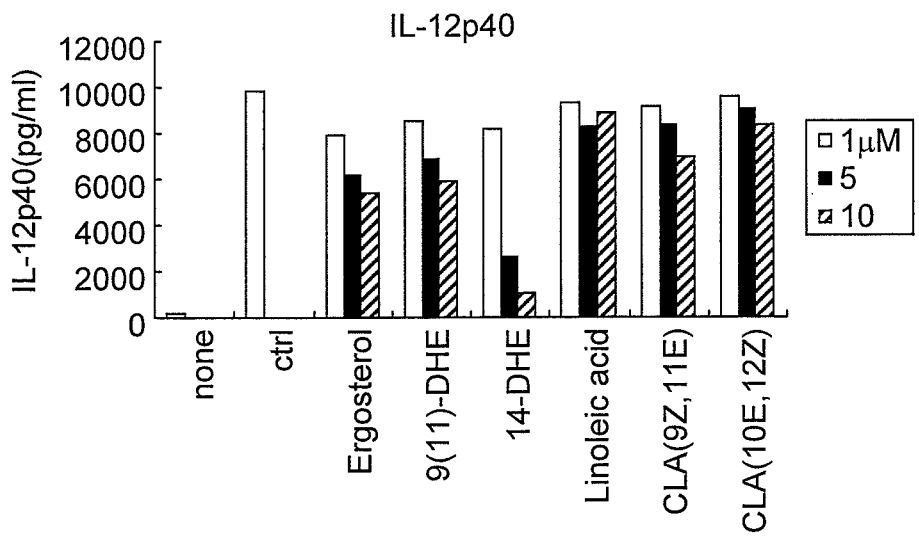

As shown in FIG. 14, the expression of an inflammatory cytokine, IL-12p40, drastically decreased with the addition of 14-DHE. Also in this case, among control substances, a slight decrease was observed with the addition of 9(11)-DHE, but the decrease was of a lesser degree than that due to 14-DHE, indicating that the effect of 9(11)-DHE was significantly inferior to that of 14-DHE. Furthermore, the expression of an anti-inflammatory cytokine, IL-10, slightly increased with the addition of 14-DHE. This suggests that 14-DHE suppresses inflammation overall so as to increase the anti-inflammatory effect.

As seen from the results of FIG. 13 and FIG. 14, although conjugated linoleic acid or the like had been reported to inhibit DC activation, the addition thereof at the concentrations employed herein did not affect the expression of the series of DC cell surface markers and cytokines. The use of these substances at 50 μM exhibited the effect reported in the prior art literatures. Hence, it was revealed that the use of 14-DHE at a concentration lower than those of the aforementioned substances exhibits the outstanding effect.

Example 10

Evaluation of Regulatory T Cell (Treg)-Inducing Capacity of DCs Treated with 14-DHE <Experimental Method>

In a manner similar to that in Example 5, the Treg-inducing activity of mDCs treated with 14-DHE was measured. Similar measurement was also performed using DCs not treated with 14-DHE as a control.

<Results>

(A) Antigen-Non-Specific Treg-Inducing Capacity (Mixed Lymphocyte Culture Reaction (MLR))

Figure 15:
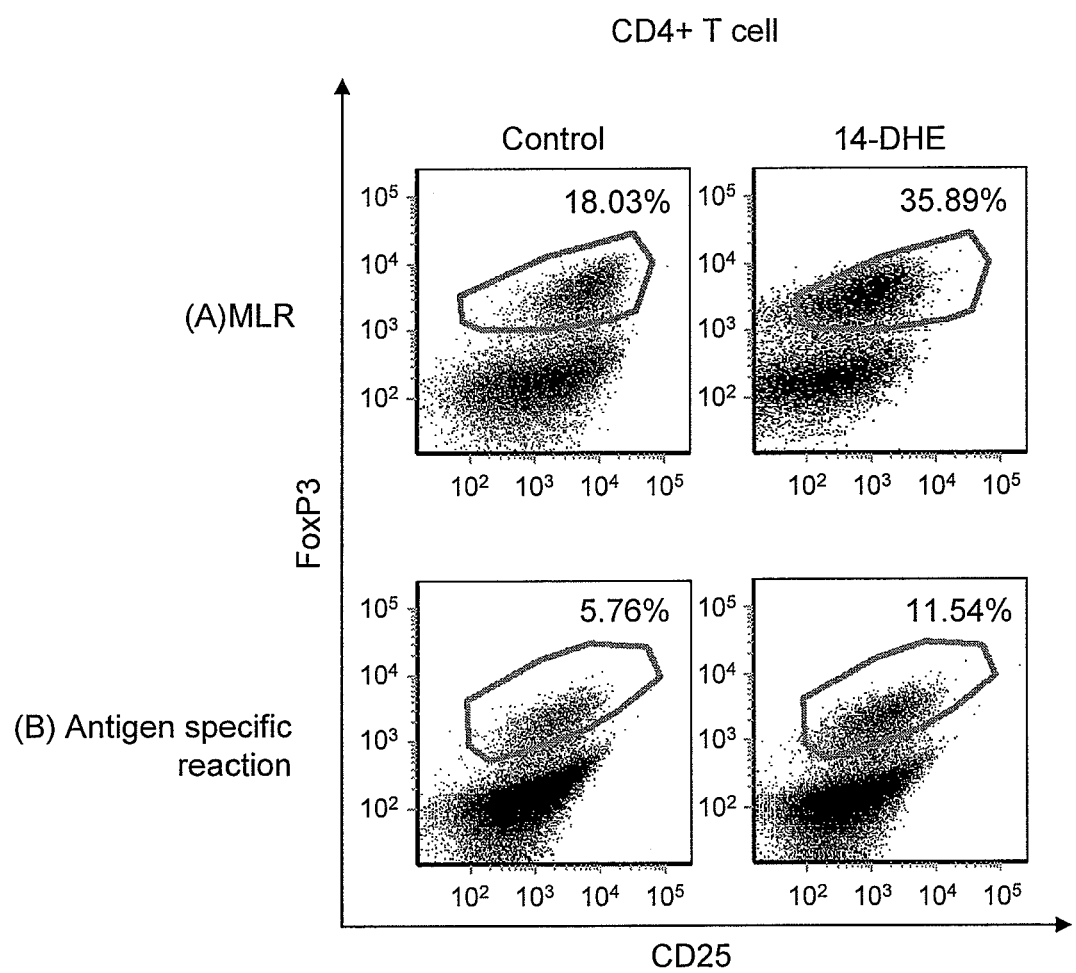
FIG. 15 shows the proportion of Treg induced by DCs treated with 14-DHE (antigen non-specific reaction (MLR) and antigen specific reaction).

As shown in FIG. 15A, the generation of Treg was found to increase about 2 times compared with the control after co-culture with DCs treated with 14-DHE.

(B) Antigen-Specific Treg-Inducing Capacity

As shown in FIG. 15B, the generation of Treg was found to increase about 2 times compared with the control after co-culture with DCs treated with 14-DHE.

The above results demonstrated that 14-DHE can enhance Treg-generating capacity by varying the properties of DCs.

Example 11

Profile of Cytokines Produced by $CD4^+$ T Cells Induced by DCs Treated with 14-DHE <Experimental Method>

(1) MLR

In a manner similar to that described in the above Examples, bone marrow cells were prepared from C57BL/6 mouse thigh bone, and then dendritic cells were induced using Flt-3L. 14-DHE was added at 3 μM simultaneously with the initiation of culture. Seven days later, *Salmonella typhosa*-derived LPS (Sigma Aldrich) was added at 5 ng/mL and then 24 hours later, cells were recovered. Subsequently, $CD11c^+CD11b^+$ was set as a gate for mDCs and then recovered cells were sorted. Next, from the BALB/c mouse spleen, $CD4^+CD62L^+$ T cells were isolated using the $CD4^+CD62L^+$ T cell isolation kit II (mouse) (Miltenyi Biotec), followed by mixed culture at a ratio of mDC:$CD4^+$T cell of 1:5. As a control, mDC prepared in the absence of 14-DHE was used. A culture supernatant on day 4 of culture was recovered, and then TNF-α, IFN-γ, IL-6, IL-10, and IL-17 were measured by ELISA. As ELISA kits, Mouse TNF-α Ready-SET-Go! (eBioscience), a BD OptEIA Mouse IFN-γ ELISA set (BD Life Science), Mouse IL-6 Ready-SET-Go! (eBioscience), a BD OptEIA Mouse IL-10 ELISA set (BD Life Science), and Mouse IL-17 DuoSet ELISA (R&D Systems) were separately used.

(2) Antigen-Specific T Cell Reaction mDCs were prepared by the method same as that in the MLR experiment. Naive $CD4^+$ T cells were prepared from OT-II mice (Charles River) in which TCR of $CD4^+$ T cells is specific for $OVA_{323-339}$ epitope on the C57BL/6 background. Mixed culture was performed at a ratio of mDC:$CD4^+$ T cell of 1:5 in the presence of 0.1 μM $OVA_{323-339}$ peptide. The culture supernatant was recovered on day 4 of culture, and then TNF-α, IFN-γ, IL-6, IL-10, and IL-17 were measured by ELISA.

<Results>

(1) MLR

Figure 16:
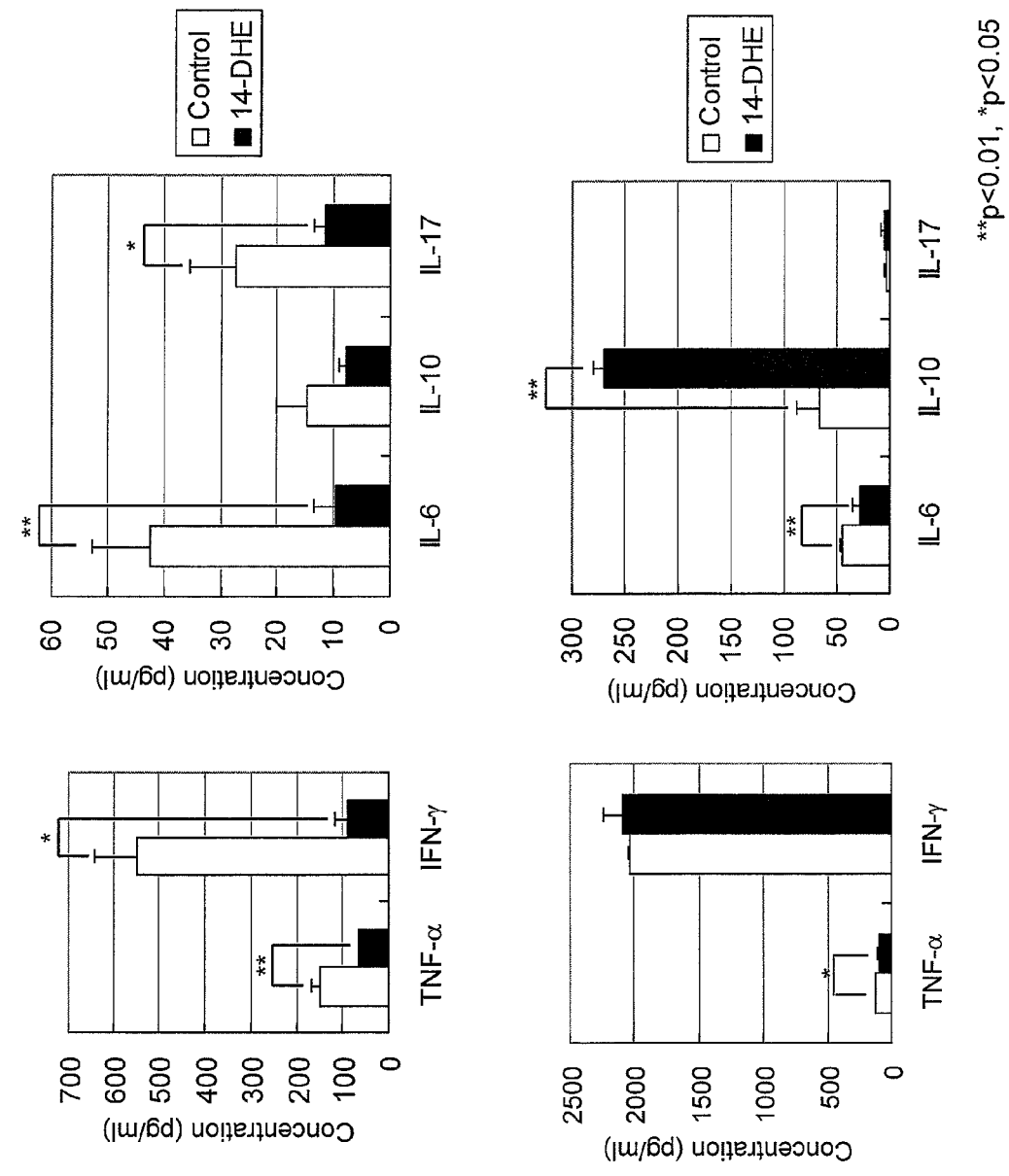
FIG. 16 shows the profiles of cytokine production from $CD4^+$ T cells induced by DCs treated with 14-DHE.

As shown in FIG. 16A, when compared with the case of the control mDC, $CD4^+$ T cells proliferated using mDCs treated with 14-DHE were observed to exhibit significant decreases in production of the inflammatory cytokines TNF-α, IFN-γ, IL-6, and IL-17. For the production of an anti-inflammatory cytokine, IL-10, no statistically significant difference was observed.

(2) Antigen-Specific T Cell Reaction

As shown in FIG. 16B, when compared with the case of control mDCs, $CD4^+$ T cells proliferated using mDCs treated with 14-DHE were observed to exhibit a significant decrease in production of TNF-α and IL-6. For the production of IFN-γ and IL-17, no statistically significant difference was observed. For the production of the anti-inflammatory cytokine IL-10, the significant increase thereof was observed.

(3) Conclusion

The above results demonstrated that the production of inflammatory cytokines decreased in the $CD4^+$ T cells proliferated with mDCs treated with 14-DHE. This suggests that 14-DHE has the effect of suppressing inflammatory response and thus this substance is thought to be useful as an anti-inflammatory agent.

Example 12

Evaluation of the $CD8^+$ Regulatory T Cell ($CD8^+$ Treg) Differentiation-Inducing Capacity of DCs Treated with 14-DHE In general, the term "Treg" often refers to a $CD4^+FoxP3^+$ regulatory T cell. However, it has been reported in recent years: that $FoxP3^+$ regulatory T cell population is present not only in $CD4^+$ T cells, but also in $CD8^+$ T cells (Cosmi, L. et al., Blood, 2003, 102 (12): 4107-14); and that the cell population exhibits a strong anti-inflammatory effect (Singh, R P. et al., J. Immunol., 1007, 178 (12): 7649-57; Chaput. N. et al., Gut, 2009, 58 (4): 520-9). As clearly demonstrated by the results of Example 10, DCs treated with 14-DHE increases $CD4^+$ regulatory T cells. In this Example, the $CD8^+$ regulatory T cell-inducing effect of DCs treated with 14-DHE was examined as described below.

<Experimental Method>

In a manner similar to Example 11, mDCs were sorted from DCs induced from C57BL/6 mouse bone marrow cells in the presence of 14-DHE and Flt-3L. Next, $CD8^+$ T cells were isolated from the BALB/c mouse spleen using the $CD8\alpha^+$ T cell isolation kit (mouse) (Miltenyi Biotec). Cells were mixed at a ratio of mDC:$CD8^+$ T cell of 1:10 and then cultured in the medium containing 0.5 ng/mL TGF-α 3 for 5 days. Five days later, the cells were recovered and then the proportion of $CD25^+FoxP3^+$ cells in $CD8^+$ T cells was determined using a flow cytometer. Prior to flow cytometry, cell staining was performed using CD8α-PE-Cy7, CD25-APC-Cy7, and CD3e-PerCP, cell membrane permeabilization treatment was performed using the FoxP3 staining buffer set (eBioscience), and then FoxP3-PE staining was performed.

<Results>

Figure 17:
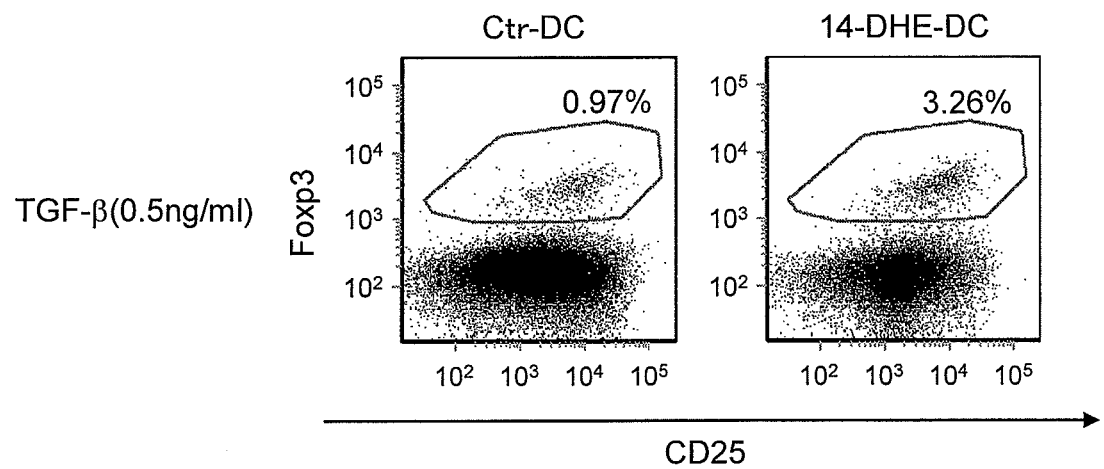
FIG. 17 shows the capacity of DCs (treated with 14-DHE) to induce differentiation of $CD8^+$ regulatory T cells ($CD8^+$ Treg), and the expression of CD25 and FoxP3 in $CD3^+CD8\alpha^+$ total $CD8^+$T cells.

As shown in FIG. 17, mDCs treated with 14-DHE induced $CD8^+CD25^+FoxP3^+$ cells to a degree 3 times or more compared with that in the case of control mDCs.

The above results demonstrated that 14-DHE has the effect of inducing not only $CD4^+$ Treg, which has been conventionally proposed, but also $CD8^+$ Treg.

Example 13

Regulatory T-Cell-Inducing Effect of 14-DHE on $CD4^+$ Naive T Cells

It was demonstrated in Examples 10 and 12 that 14-DHE changes the characteristics of DCs so that 14-DHE indirectly exhibits the effect of inducing regulatory T cells. In this Example, in order to reveal whether or not 14-DHE could directly act on T cells to induce regulatory T cells, 14-DHE was caused to directly act on naive $CD4^+$ T cells and the induction of $CD25^+FoxP3^+$ cells was examined.

<Experimental Method>

Naive $CD4^+$ T cells were isolated from BALB/c mouse spleen-derived cells using the $CD4^+CD62L^+$ T cell isolation kit II (mouse) (Miltenyi Biotec). $CD4^+$ T cells were seeded at a density of $5\times10^5$ cells/mL to 48-well plates ($2.5\times10^5$ cells per well), and then 1 μg/mL anti-CD3 antibody and 0.2 μg/mL anti-CD28 antibody were added. At this time, 2 types of media (i.e., media with and without TGF-β) were used. 14-DHE was added at a concentration of 0, 50, 100, 500, and 1000 nM. Five days later, cells were recovered. The proportion of $CD25^+FoxP3^+$ cells in $CD4^+$ T cells was determined using a flow cytometer. Prior to flow cytometry, cell surface staining was performed using CD4-APC, CD25-FITC and CD3e-PerCP, cell membrane permeabilization treatment was performed using the FoxP3 staining buffer set (eBioscience), and then FoxP3-PE staining was performed.

<Results>

Figure 18:
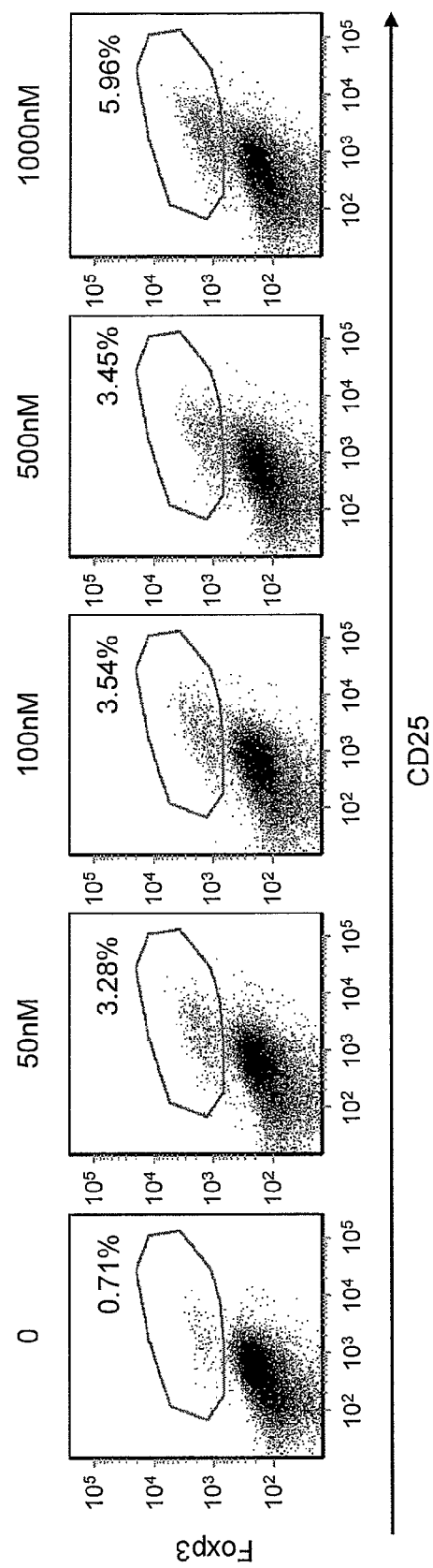
FIG. 18 shows the Treg-inducing effect of 14-DHE on naive T cells, and the expression of CD25 and FoxP3 in $CD3^+CD4^+$ total $CD4^+$ cells. Treatment with 14-DHE was performed at a concentration of 50 nM, 100 nM, 500 nM, or 1000 nM.

As shown in FIG. 18, no change in the proportion of $CD25^+FoxP3^+$ cells due to the addition of 14-DHE was observed in the absence of TGF-β. In the presence of TGF-β, the addition of 14-DHE at the lowest concentration of 50 nM resulted in an increase in the proportion of $CD25^+FoxP3^+$ cells, which was 5 times or more compared with that when no 14-DHE was added.

From the above results, it was revealed that 14-DHE can act not only on DCs to alter the characteristics thereof, but also directly on T cells so as to be able to induce Treg. The effective concentration is lower by 20 times or more compared with that of DCs (1 μM). This demonstrates that the susceptibility of T cells to 14-DHE is higher than that of DCs to the same. Also, this suggests that when 14-DHE is administered to a human, the dose thereof can be significantly reduced.

Example 14

Timing and Duration of the DC-Activation-Suppressing Effect of 14-DHE

In the experiment of Example 9 in which 14-DHE was revealed to have regulatory DC induction activity, 14-DHE was added simultaneously with the initiation of DC differentiation and existed until the final step of LPS induction. Hence, which stage of DC differentiation 14-DHE acts on, as well as what time the duration of the effect is, remained unknown. Thus, in this Example, the following factors were examined: (1) when the addition of 14-DHE was begun at the initiation of the induction of DC differentiation, the time required for obtaining the effect; (2) whether or not the effect could be obtained with the addition of 14-DHE even after the initiation of DC differentiation; and (3) the length of the duration of the effect.

<Experimental Method>

In a manner similar to those of the Examples above, C57BL/6 mouse bone marrow cells were prepared and then DCs were induced using Flt-3. The concentration of the added 14-DHE was 3 μM in all cases. The drug residence time in the culture system was controlled by medium exchange. Inflammation was induced using 5 ng/mL LPS, and then the expression level of CD86 was measured using a flow cytometer, so that the characteristics of regulatory DCs were determined. At this time, the cells that had been treated with LPS and without 14-DHE were used as control cells. The median fluorescence intensity (Median Fluorescence Intensity: MFI) of CD86 in the cells treated with 14-DHE was divided by MFI of untreated cells. The determined values indicate: 1 or more, no effect (score: −); 0.7-0.99, weak effect (score: +); 0.4-0.69, moderate effect (score: ++); and 0.4 or less, strong effect (score: +++).

<Results>

Figure 19:
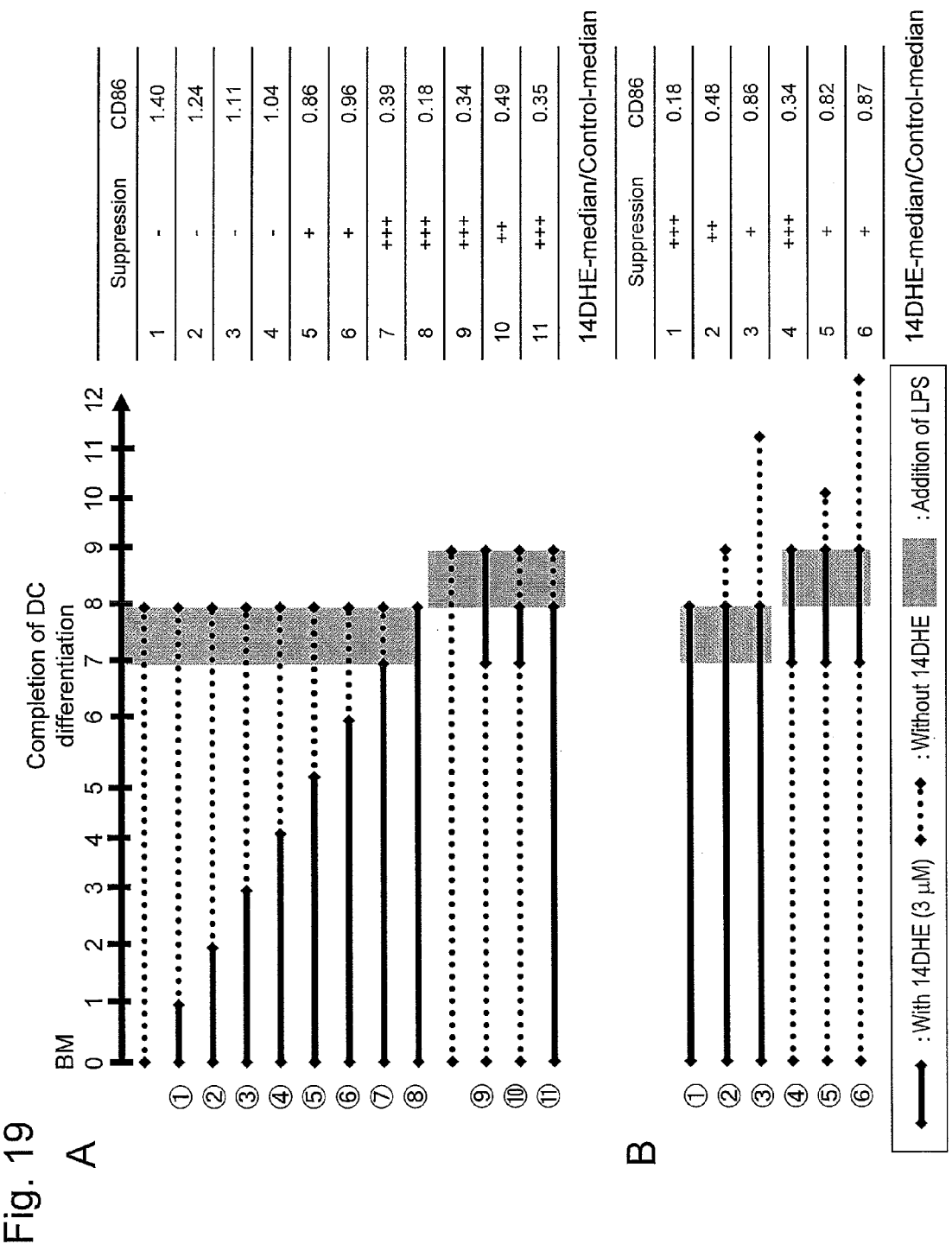
FIG. 19 shows the timing for 14-DHE to exhibit the DC activation-suppressing effect and the duration of the effectiveness of 14-DHE.

The results are shown in FIG. 19. As shown in FIG. 19A 1-8, it was demonstrated that when the addition of 14-DHE is begun at the initiation of DC differentiation, 14-DHE should be added for 7 days starting from the initiation of differentiation in order to obtain a strong effect. The effect can be observed by 5 or 6 days of the addition thereof, but the degree of the effect significantly decreased.

As shown in FIG. 19A 9-11, it was revealed that even when the addition of 14-DHE was begun on day 7 when DC differentiation was completed, strong effect was obtained at the same degree as in the case that the addition was begun on day 0. Also, when 14-DHE was absent at the time of adding LPS, decrease in the effect was observed. This suggests that the effect of 14-DHE may occur at the time of inflammation induction.

In FIG. 19B, the duration of the effect of 14-DHE was examined. It was demonstrated that in both the case that the addition of 14-DHE was begun on day 0 and the case that the addition of 14-DHE was begun on day 7, the effect significantly decreased within 72 hours.

From the above results, it was demonstrated that: (1) the time required for 14-DHE to exhibit its effect is preferably 7 or more days; (2) 14-DHE exhibits an effect of suppressing the inflammatory reaction on differentiated DCs, and, the presence of 14-DHE during inflammatory stimulation is important; and (3) the duration of the effect is 72 hours.

From these results, it was suggested that, when 14-DHE is administered to a human, 14-DHE functions as an anti-inflammatory agent that acts on DCs already existing in vivo so as to attenuate inflammatory stimuli.

Example 15

Effect of 14-DHE on Multiple Sclerosis Model

The above Example proved that 14-DHE has an in vitro anti-inflammatory effect. To further verify the in vivo anti-inflammatory effect, 14-DHE was administered to the multiple sclerosis model mouse (Experimental Autoimmune Encephalomyelitic; EAE) that has often been used as an autoimmune disease model.

<Experimental Method>

Eight-week-old female C57BL/6 mice were divided into the following 2 groups at 5 mice per group:
(1) Vehicle Group
(2) 14-DHE Group (10 μg/Animal)

On day 0, the 35-55 peptide (MOG35-55, Operon), a glycoprotein of myelin oligodendroglial cells, as an antigen was mixed with complete Freund's adjuvant (CFA, Difco) and then the mixture was subcutaneously administered at a dose of 200 μg/animal. Subsequently, pertussis toxin (Wako Pure Chemical Industries, Japan) was intraperitoneally administered at a dose of 200 ng/animal on day 1 and day 3, thereby inducing the onset of multiple sclerosis. During days 7 to 18, 14-DHE was intraperitoneally administered at a dose of 10 μg/animal once a day. To the vehicle group, the following solvent for 14-DHE was administered: 10% ethanol (Wako Pure Chemical Industries, Japan)/10% Cremophor (Wako Pure Chemical Industries, Japan)/80% PBS (Takara, Japan).

During the experimental period (i.e., during days 0 to 20), disease score was determined based on the following criteria:
Score 0: Normal
Score 1: Unable to freely move tail
Score 2: Unable to normally walk
Score 3: Paralysis of one hindlimb
Score 4: Paralysis of both hindlimbs
Score 5: Paralysis of forelimbs and hindlimbs
Score 6: Death Mice were autopsied on day 11 (when inflammation was thought to take place in vivo) to obtain biochemical data.

(1) Spleen cells were prepared and then cultured for 7 days with or without re-stimulation with 2 μM MOG. Culture supernatants were recovered. The amounts of produced IFN-γ and TNF-α were measured by ELISA.

(2) Spleen cells and regional lymph node (inguinal or axillary) cells were prepared and then cultured for 3 days with re-stimulation with 2 μM MOG. Golgi plug (1 μL/mL) (Becton, Dickinson and Company) was added and then further incubation was performed for 4.5 hours. Cells were recovered and then subjected to cell surface staining with CD4-PerCP and CD3-APC-Cy7. Next, cell membrane permeabilization treatment was performed using the Cytofix/CytoPerm kit (Becton, Dickinson and Company), intracellular cytokine staining was performed using antibodies to TNF-α-FITC, IL-17-PE, IL-10-APC, and IFN-γ-PE-Cy7, and then the positive rate of intracellular cytokines in $CD4^+$ T cells was measured using FACS.

(3) Regional lymph node cells and spleen cells were stained using the CellTrace CFSE Proliferation kit (Molecular Probes). The stained cells were seeded at a concentration of $1 \times 10^6$ cells/mL and then cultured for 3 days with stimulation with 2 μM MOG. Cells were recovered, stained with CD3-PerCP and CD4-APC, and then subjected to FACS analysis. Cell proliferation was evaluated as a proportion of cells with decreased CFSE fluorescence intensity in all cells.

(4) To evaluate mDC activation in regional lymph node cells and spleen cells, the cells were stained with FITC-I-A/I-E (MHC class II), PE-CD86, PerCP-B220, APC-CD80, APC-Cy7-CD11b, and PE-Cy7-CD11c. A gate was set on mDCs, which are $CD11b^+CD11c^+B220^-$ cells, and I-A/I-E (MHC class II), CD86, and CD80 were measured as activation markers.

<Results>

Figure 20:
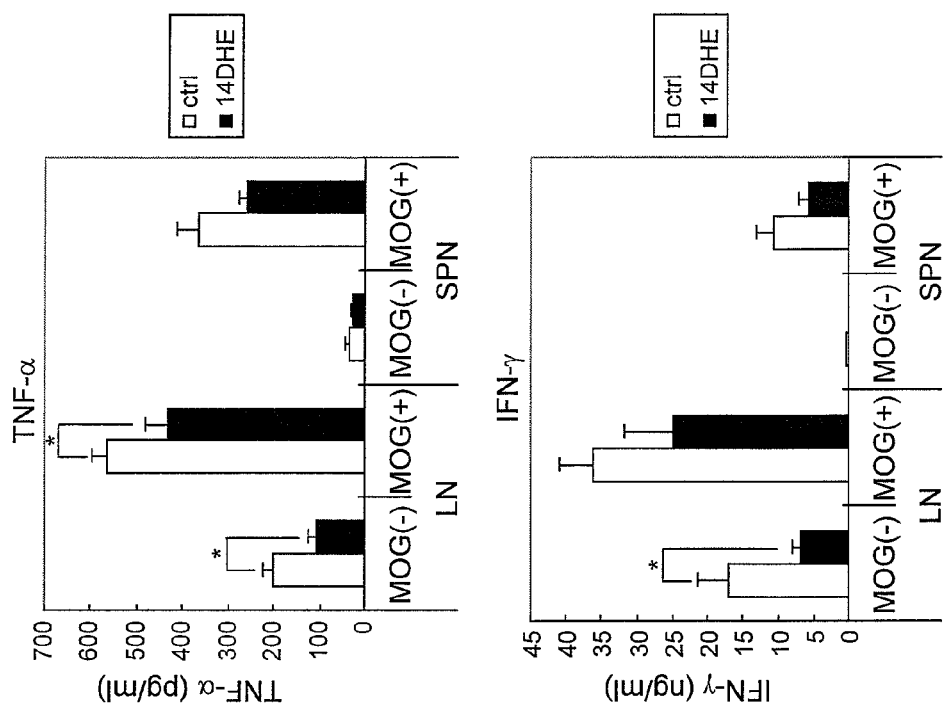
FIG. 20 shows the effect of 14-DHE on multiple sclerosis.
Figure 20:
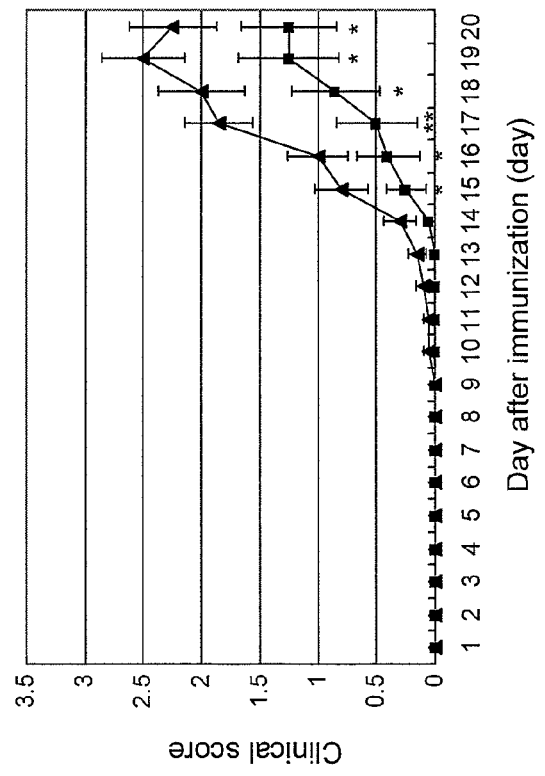
Figure 20:
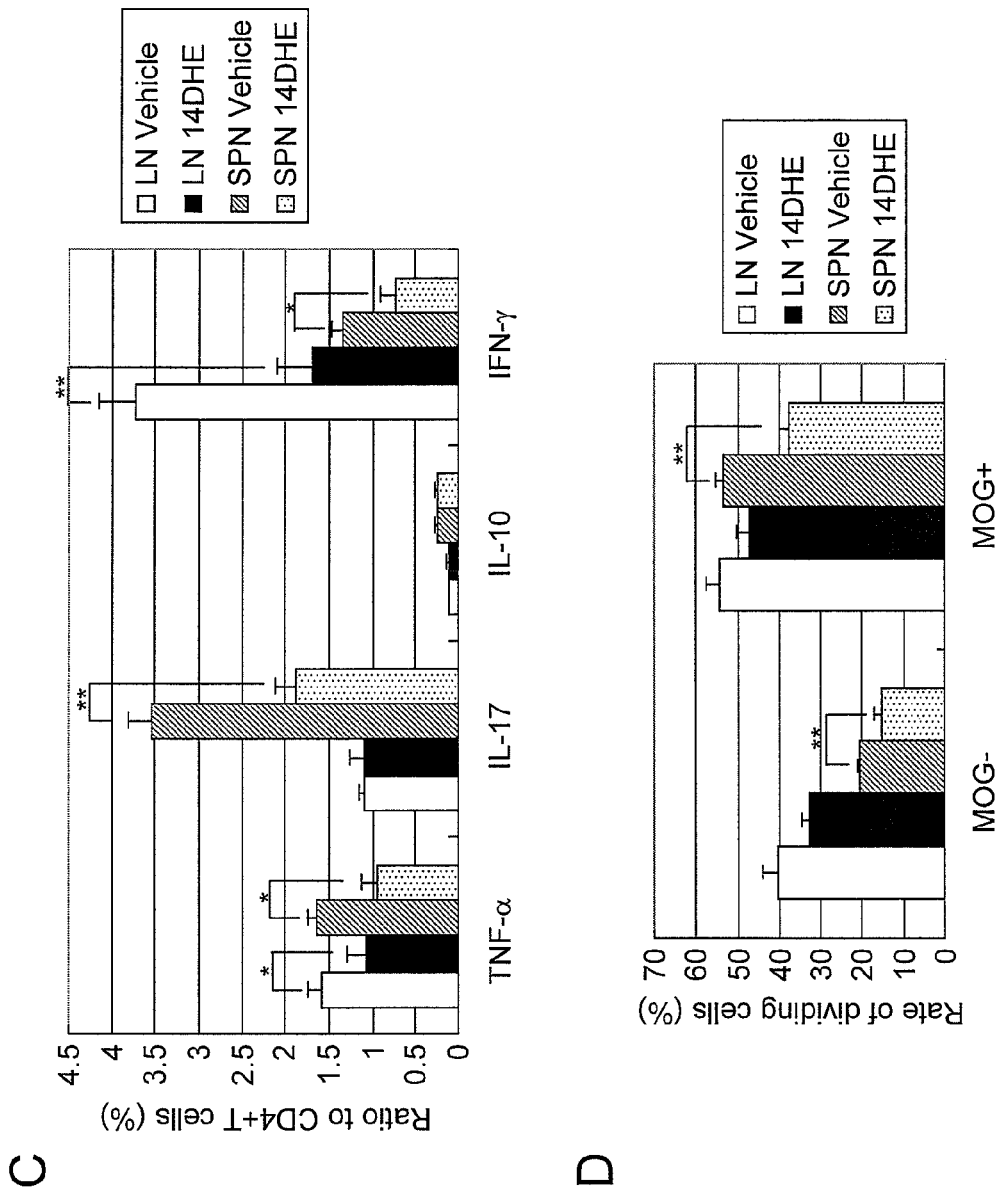
Figure 20:
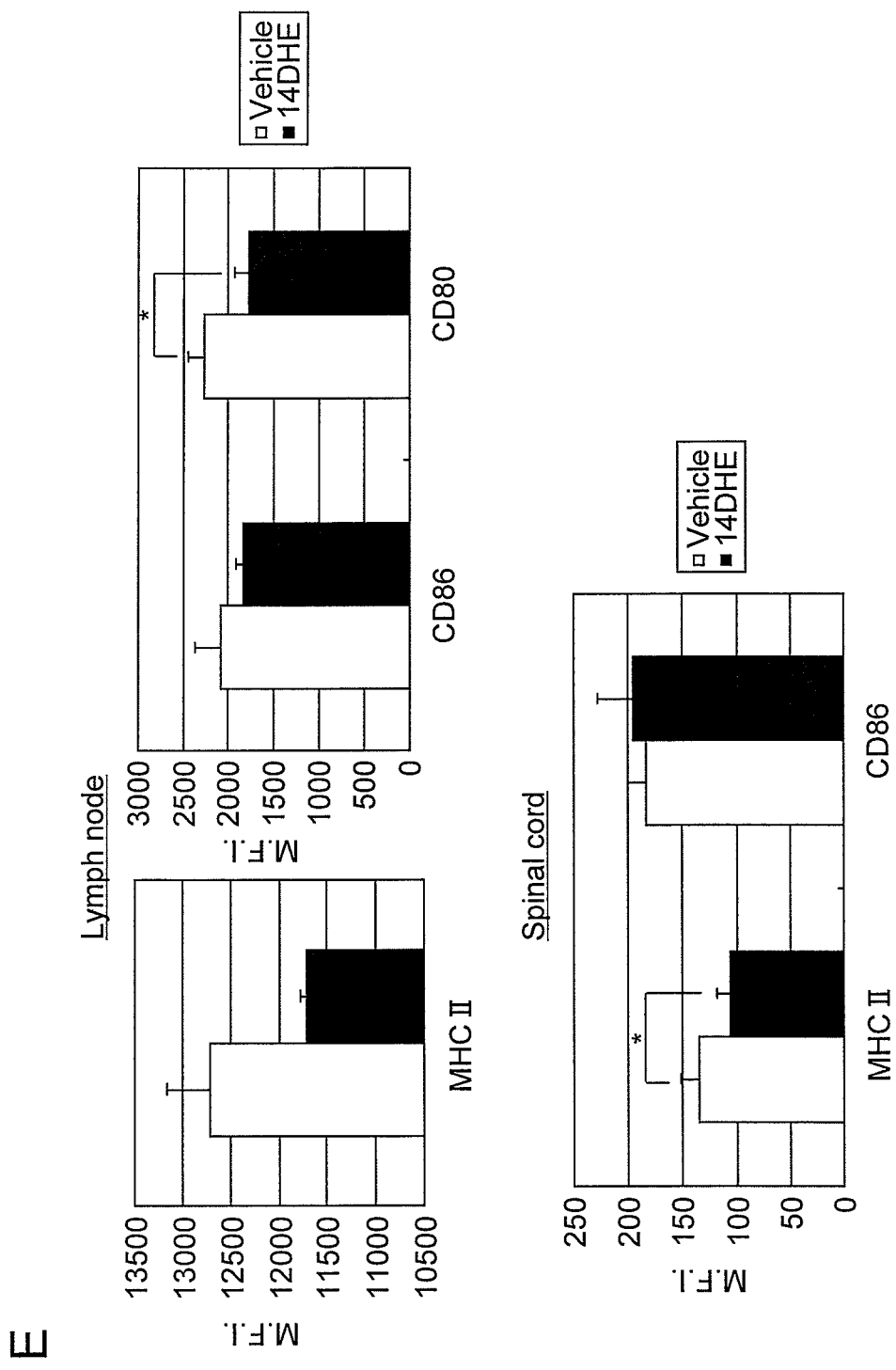

The results are shown in FIG. 20. In FIG. 20A, in the group to which 14-DHE had been administered, decreases were confirmed in all of accumulated disease score, maximum score, and incidence. In addition, delayed onset was also observed.

FIG. 20B shows the amounts of inflammatory cytokines produced from regional lymph node cells and spleen cells on day 11. In the group to which 14-DHE had been administered, the production of the inflammatory cytokine TNF-α significantly decreased in regional lymph node cells regardless of whether or not re-stimulation with the MOG antigen was conducted. TNF-α production from spleen cells that had been re-stimulated with the MOG antigen also decreased. IFN-γ production was observed to significantly decrease in the case that the regional lymph node cells were not re-stimulated with the MOG antigen; and a decreasing trend was observed in both types of cells in the case of re-stimulation with the MOG antigen.

FIG. 20C shows cytokine production by CD4+ T cells in regional lymph node cells and spleen cells. Both TNF-α production and IFN-γ production were observed to significantly decrease in both lymph node cells and spleen cells of the group to which 14-DHE had been administered. Also, the production of IL-17 was observed to significantly decrease in spleen cells by administration of 14-DHE.

FIG. 20D shows the proliferation rate of CD4+ T cells in regional lymph node cells and spleen cells. In spleen cells, a significant decrease was observed in the group to which 14-DHE had been administered, regardless of whether or not re-stimulation with the MOG antigen was conducted. Also, a decreasing trend was observed in lymph node cells. These results demonstrated that the proliferation of inflammatory T cells was suppressed by administration of 14-DHE.

FIG. 20E shows the activation of mDCs (antigen presenting cells) in the lymph node and the spinal cord at the time of autopsy on day 11. In the lymph node, a decreasing trend was observed for I-A/I-E (MHC class II) and CD86, which are the indicators for DC activation, and a significant decrease was observed for CD80. In the spinal cord, a significant decrease was observed for I-A/I-E. From these results, it can be speculated that the proliferation of inflammatory T cells is suppressed by 14-DHE through inactivation of antigen-presenting cells.

The above results demonstrated that 14-DHE also has the effect of suppressing autoimmune diseases including multiple sclerosis, in vivo.

Example 16

Human Regulatory DC-Inducing Activity of 14-DHE

It was revealed in the above Example that 14-DHE can cause decreases in the expression levels of maturation factors on the cell surfaces of mouse DCs. In this Example, the effect of 14-DHE on human DCs was evaluated as described below.
<Experimental Method>

Mononuclear cells were prepared from human peripheral blood by density-gradient centrifugation using Ficoll-Paque (GE Healthcare, Japan). These cells were subjected to positive selection using anti-human CD14 MACS beads (Miltenyi Biotec), so that CD14-positive cells were obtained. CD14-positive cells were cultured in RPMI1640 media (containing 10% FBS (Invitrogen), 50 μmol/L 2-mercaptoethanol (Wako Pure Chemical Industries, Japan), 50 U/mL penicillin, and 50 μg/mL streptomycin (Gibco) (Sigma Aldrich)) supplemented with recombinant human GM-CSF (800 U/mL, Leukine, Berlex) and recombinant human IL-4 (100 ng/mL, Peprotech). During culture, medium exchange was performed once every 2 days. On day 7 of culture, 14-DHE was added at a concentration of 1 μM, 3 μM, or 10 μM. To a control, 10 μM ergosterol, which was a related substance, was added. Also, to a negative control, 1% ethanol, which was a solvent for 14-DHE, was added. The cells were recovered on day 8 of culture, counted, and then suspended at a density of 3×10^5 cells/mL in the above media. To cell suspensions, 1 μg/mL LPS and 100 ng/mL IFN-γ (both, Sigma Aldrich), or cytokine cocktail (1 μg/mL PGE$_2$ (Sigma Aldrich), 10 ng/mL TNF-α,  2 μg/mL IL-6, and 10 ng/mL IL-1β (3 (all, BD Bioscience)) were added, followed by 24-hour culture. After culture, the cells were stained for CD86, HLA-DR, and CD80. Antibodies used were all produced by BD Bioscience. The gate of DCs was set by FSC and SSC, and the expression levels of these cell surface markers were analyzed.
<Results>

Figure 21:
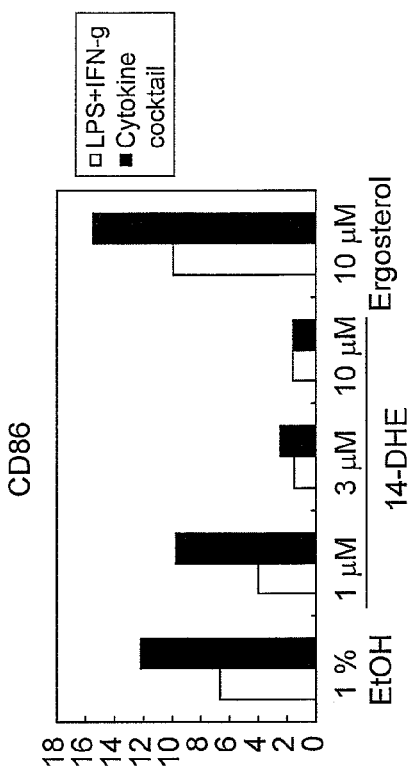
FIG. 21 shows the effect of 14-DHE on the expression of maturation factors on the cell surfaces of human DCs.
Figure 21:
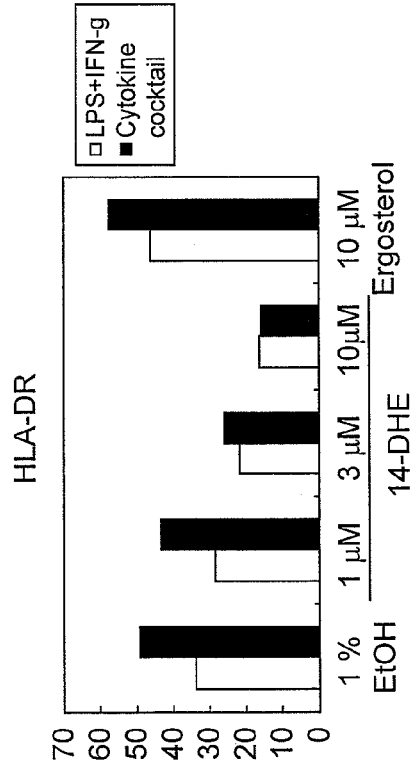
Figure 21:
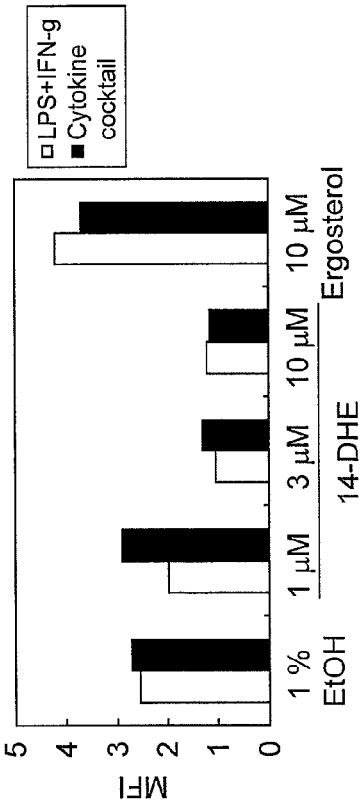

As shown in FIG. 21, the expression levels of the MHC class II molecule HLA-DR and the costimulatory molecules CD80 and CD86 on the cell surfaces of human DCs decreased by treatment with 14-DHE. Ergosterol as a control did not affect the expression levels of these molecules on the cell surfaces.

From the above results, it was revealed that 14-DHE has an effect of suppressing the expression of maturation factors on the cell surfaces of also human DCs.

These experimental results obtained using 14-DHE strongly support the fact that the immunomodulatory effect of processed fermented products of cereal plant-derived materials that were proven in the above Examples, results from 14-DHE. The experimental results also demonstrate that 14-DHE can be used as a novel immunomodulator.

INDUSTRIAL APPLICABILITY

According to the present invention, novel food-derived materials that can be used for prevention and improvement of inflammatory reactions are provided. Thus, the present invention is useful in the fields of health science, medicine, and foods.

All publications, patents, and patent applications cited herein are incorporated herein by reference in their entirety.

The invention claimed is:

1. A method for modifying an antigen presenting cell, said method comprising contacting an antigen-presenting cell with ergosta-5,7,14,22-tetraen-3β-ol represented by the following chemical formula:

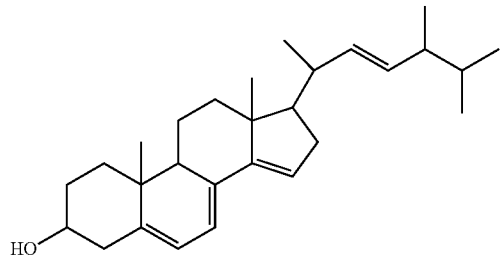 [SMILES: CC(C)C(C)/C=C/C(C)C1CC=C2C3=CC=C4CC(O)CCC4(C)C3CCC21C]

to modify the antigen-presenting cell and thereby to produce a modified antigen-presenting cell having: (i) reduced production of activated cell surface markers and inflammatory cytokines as compared to the unmodified antigen-presenting cell; and (ii) an ability of inducing regulatory T cells.

2. The method according to claim 1, wherein the antigen-presenting cell is a dendritic cell.

3. The method according to claim 1, further comprising the step of allowing the modified antigen-presenting cell to induce a naive CD4+ T-cell to become a regulatory T-cell.

* * * * *